US011622586B2

(12) United States Patent
Chacko

(10) Patent No.: US 11,622,586 B2
(45) Date of Patent: Apr. 11, 2023

(54) PATIENT FACE MASK FOR IDENTIFYING VACCINATION STATUS AND CONTROLLING MOVEMENT WITHIN A MEDICAL FACILITY

(71) Applicant: Cherackal Chacko, Portland, CT (US)

(72) Inventor: Cherackal Chacko, Portland, CT (US)

( * ) Notice: Subject to any disclaimer, the term of this patent is extended or adjusted under 35 U.S.C. 154(b) by 0 days.

(21) Appl. No.: 17/384,693

(22) Filed: Jul. 23, 2021

(65) Prior Publication Data

US 2022/0295912 A1    Sep. 22, 2022

Related U.S. Application Data

(60) Provisional application No. 63/207,696, filed on Mar. 16, 2021.

(51) Int. Cl.

| G06Q 10/10 | (2023.01) |
| G06Q 40/08 | (2012.01) |
| G06Q 10/06 | (2023.01) |
| A41D 1/00 | (2018.01) |
| A41D 13/11 | (2006.01) |
| G16H 10/60 | (2018.01) |
| G08B 5/22 | (2006.01) |
| G16H 40/20 | (2018.01) |

(Continued)

(52) U.S. Cl.
CPC .............. *A41D 1/002* (2013.01); *A41D 13/11* (2013.01); *A41D 27/08* (2013.01); *G06Q 50/265* (2013.01); *G07C 9/38* (2020.01); *G08B 5/22* (2013.01); *G16H 10/60* (2018.01); *G16H 40/20* (2018.01)

(58) Field of Classification Search
CPC ........ A41D 1/002; A41D 13/11; A41D 27/08; G07C 9/38; G08B 5/22; G16H 10/60; G16H 40/20; G06Q 50/265
USPC .................................................. 705/1.1–912
See application file for complete search history.

(56) References Cited

U.S. PATENT DOCUMENTS 3,220,409 A * 11/1965 Liloia ................ A41D 13/1146
                                                    128/206.19
4,488,547 A * 12/1984 Mason ................... A41D 13/11
                                                    116/206

(Continued)

FOREIGN PATENT DOCUMENTS

CN         210747391          6/2020
WO    WO-2022036303 A1 *     2/2022

OTHER PUBLICATIONS

Perez-Pena, Vaccine Passports: What Are They, and Who Might Need One?, The New York Times, https://www.nytimes.com/2021/04/09/world/europe/virus-vaccine-passport.html, Apr. 9, 2021, The New York Times Company, New York United States.
Solo L16BL-0100 12-24 oz. Translucent Flat Plastic Lid with Straw Slot and Identification Buttons—2000/Case, WebstaurantStore, https://www.webstaurantstore.com/dart-solo-l16bl-0100-12-24-oz-translucent-flat-plastic-lid-with-straw-slot-and-identification-buttons-case/760L16BL.html, webpage content previously viewed and available in Apr. 2021, retrieved Aug. 19, 2021, p. 1, Lancaster United States.
Choice 16"×16"×2" Kraft Corrugated Pizza Box—50/Case, WebstaurantStore, https://www.webstaurantstore.com/16-x-16-x-1-3-4-kraft-corrugated-pizza-boxcase/245CPB16GRN.html, webpage content previously viewed and available in Apr. 2021, retrieved Aug. 19, 2021, p. 1, Lancaster United States.

(Continued)

*Primary Examiner* — Jonathan P Ouellette
(74) *Attorney, Agent, or Firm* — Law Office of John B. Hudak, PLLC; John Brian Hudak

(57) ABSTRACT

A face mask which displays information to another person. The facemask can display medical information. Specifically, the medical information displayed can be the vaccination status of the wearer, where the vaccination status of the wearer relates to the number of doses received for a vaccine regime of the vaccine which is used to prevent the spread of an infectious disease causing a pandemic. Markings on the outer surface of the face covering structure of the face mask convey the information.

8 Claims, 15 Drawing Sheets

Figure 1:
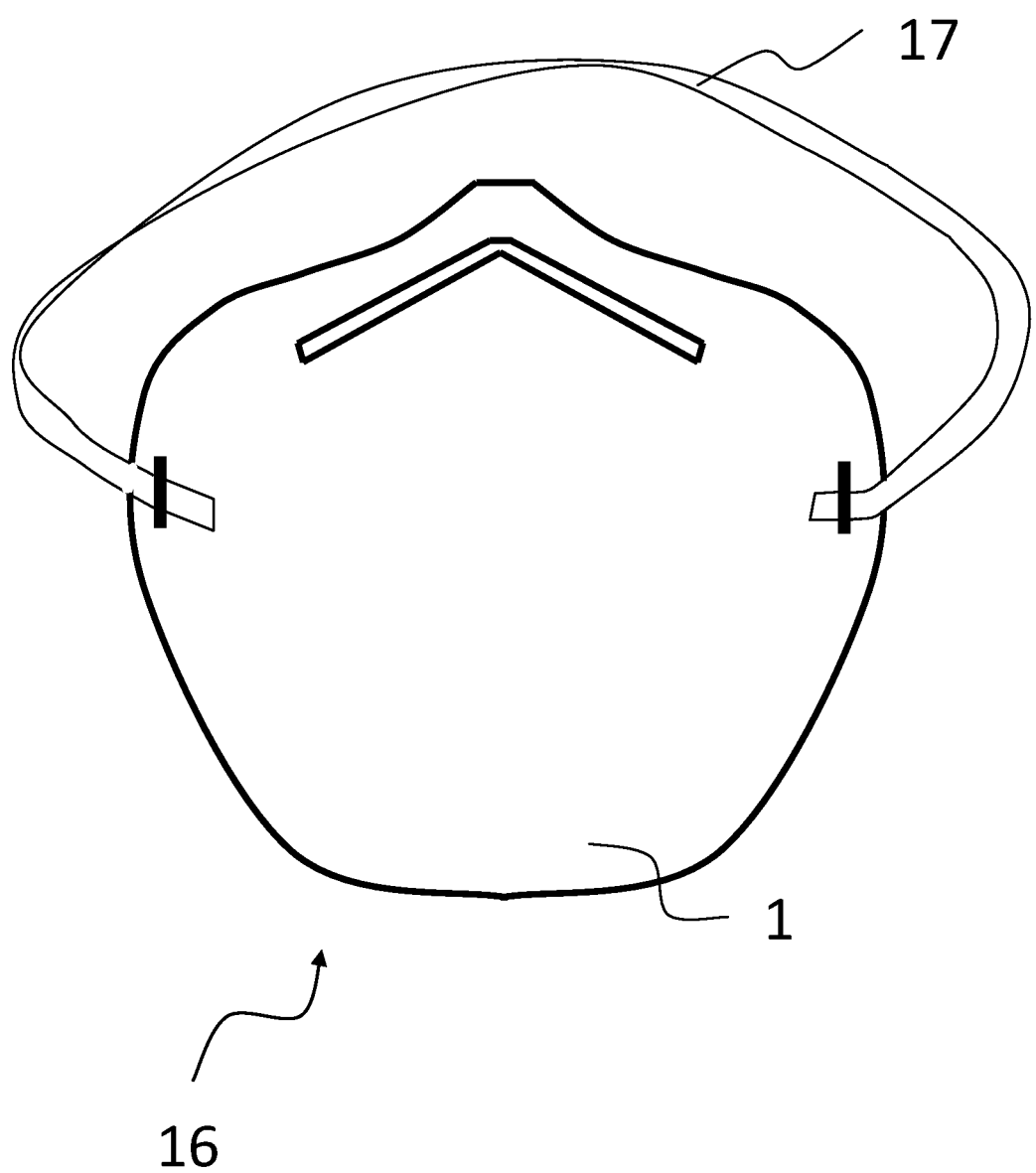

(51) Int. Cl.
  *A41D 27/08* (2006.01)
  *G07C 9/38* (2020.01)
  *G06Q 50/26* (2012.01)

(56) References Cited

U.S. PATENT DOCUMENTS

| | | | | |
|---|---|---|---|---|
| 4,856,509 | A * | 8/1989 | Lemelson | A41D 13/1146 128/206.19 |
| 5,026,084 | A | 6/1991 | Pasfield | |
| 6,023,864 | A | 2/2000 | Liebenow | |
| 6,412,486 | B1 * | 7/2002 | Glass | A41D 13/11 128/205.27 |
| 6,758,215 | B2 * | 7/2004 | Begum | A41D 13/1161 128/202.15 |
| 7,128,258 | B1 * | 10/2006 | Harper | G16H 10/65 235/375 |
| 8,662,388 | B2 | 3/2014 | Belkin | |
| D735,418 | S | 7/2015 | De Castro | |
| 10,420,383 | B2 | 9/2019 | Lewis | |
| 10,470,842 | B2 | 11/2019 | Moore | |
| 10,486,001 | B1 * | 11/2019 | Bailey | A41D 13/1115 |
| 10,945,469 | B1 | 3/2021 | Rosenberg | |
| 10,945,470 | B1 | 3/2021 | Maroofian | |
| 10,952,639 | B2 | 3/2021 | Inoue | |
| 10,953,181 | B2 | 3/2021 | Hallett | |
| 2006/0042139 | A1 | 3/2006 | Mendes | |
| 2006/0144404 | A1 * | 7/2006 | Callan | G09F 21/02 128/206.28 |
| 2007/0199567 | A1 * | 8/2007 | Kanzer | A62B 18/025 128/206.28 |
| 2008/0230066 | A1 * | 9/2008 | Chandaria | A41D 13/11 128/206.13 |
| 2008/0313939 | A1 * | 12/2008 | Ardill | G09F 3/02 40/329 |
| 2009/0056177 | A1 | 3/2009 | Mallozzi | |
| 2009/0255535 | A1 * | 10/2009 | Kanzer | A62B 18/025 128/206.14 |
| 2010/0218774 | A1 * | 9/2010 | Flaherty | A41D 13/1138 128/863 |
| 2012/0111330 | A1 * | 5/2012 | Gartner | A61M 16/161 128/205.23 |
| 2013/0179188 | A1 * | 7/2013 | Hyde | G06Q 10/10 705/3 |
| 2015/0071978 | A1 * | 3/2015 | Chang | A61N 2/06 424/402 |
| 2019/0125011 | A1 * | 5/2019 | Eisenbrey | G01K 13/20 |
| 2020/0279464 | A1 * | 9/2020 | Llewelyn | G06F 3/147 |
| 2021/0012869 | A1 * | 1/2021 | Kotlarz | G16H 15/00 |
| 2021/0043311 | A1 * | 2/2021 | Grant | G16H 50/20 |
| 2021/0319863 | A1 * | 10/2021 | Rajagopal | G06F 21/32 |
| 2021/0326474 | A1 * | 10/2021 | Sparks | G06Q 10/10 |
| 2021/0350649 | A1 * | 11/2021 | Jafri | H04W 12/64 |
| 2021/0386134 | A1 * | 12/2021 | Plank | A41D 13/1192 |
| 2021/0391041 | A1 * | 12/2021 | White | H04L 9/3231 |
| 2022/0133432 | A1 * | 5/2022 | Guirguis | G09F 3/0297 40/633 |

OTHER PUBLICATIONS

Fully Vaccinated Adult Cloth Face Mask, Zazzle, https://www.zazzle.com/fully_vaccinated_adult_cloth_face_mask-256037838607625887, webpage content previously viewed and available in Mar. 2021, retrieved Aug. 20, 2021, Reno United States.

Pro-Vaccine, Vaccinated AF, Vaccinated Trucker Hat, Zazzle, https://www.zazzle.com/pro_vaccine_vaccinated_af_vaccinated_trucker_hat-148832763407410120, webpage content previously viewed and available in Mar. 2021, retrieved Aug. 20, 2021, Reno United States.

Fannypack, Zazzle, https://www.zazzle.com/pd/spp/pt-capsac_fannypack?tdid=e13d6137-6681-4d00-a200-b4a363556ca0, webpage content previously viewed and available in Mar. 2021, retrieved Aug. 20, 2021, Reno United States.

"I Got My COVID-19 Vaccine" Men's T-Shirt, Zazzle, https://www.zazzle.com/i_got_my_covid_19_vaccine_mens_t_shirt-235293671854226758, webpage content previously viewed and available in Mar. 2021, retrieved Aug. 20, 2021, Reno United States.

I've been vaccinated for covid-19 premium face mask, Zazzle, https://www.zazzle.com/ive_been_vaccinated_for_covid_19_premium_face_mask-256252581931468774, webpage content previously viewed and available in Mar. 2021, retrieved Aug. 20, 2021, Reno United States.

Premium Covid-19 Vaccinated Silicone Wristband—2-Pack Adult Size Bracelet—for Vaccination Identification, Brand: Solstice Accessories, Amazon, https://www.amazon.com/PREMIUM-COVID-19-VACCINATED-SILICONE-WRISTBAND/dp/B08JCXBVBN/ref=pd_Ipo_2?pd_rd_i=B08JCXBVBN&psc=1, similar webpage content previously viewed and available in Mar. 2021, current retrieved Aug. 20, 2021, Seattle United States.

Vaccinated (Green) with Custom Dates Button, Zazzle, https://www.zazzle.com/vaccinated_green_with_custom_dates_button-145516729875473357, webpage content previously viewed and available in Mar. 2021, copy retrieved Aug. 20, 2021, Reno United States.

2021 I was Vaccinated Disposable Face Mask for Adult 3 Ply Indoor Outdoor Use, Brand: CddeGuan, Amazon, https://www.amazon.com/Vaccinated-Disposable-Face_Mask-Indoor-Outdoor/dp/B08SM7XC99/ref=pd_sbs_5/142-2896415-4301401?pd_rd_w=mJaBy&pf_rd_p=0f56f70f-21e6-4d11-bb4a-bcdb928a3c5a&pf_rd_r=1P4A08MZJCR0SKPEXW0M&pd_rd_r=fb0606b0-e45e-46cd-b429-351a888da781&pd_rd_wg=0MvNu&pd_rd_i=B08SM7XC99&psc=, similar webpage content previously viewed and availabe in Mar. 2021, current copy retrived Aug. 20, 2021, Seattle United States.

* cited by examiner 51    50

48
49
48

46
47
46

FIG. 20

A patient is viewed while wearing a face mask, where the patient is at a distance greater than 6 feet from the viewer.

A vaccination status is indicated by the markings on the outer surface of the face covering structure of the face mask.

The patient is directed to an area of the medical facility designated for patients with the vaccination status indicated on the face covering structure.

The identity of the patient is determined.

The identity of the patient is entered into a database which prompts the return of the inputted vaccination status of the patient as recorded in the database.

If the vaccination status indicated on the face covering structure does not match the returned inputted vaccination status indicated in the database, the patient is moved to another area in the medical facility.

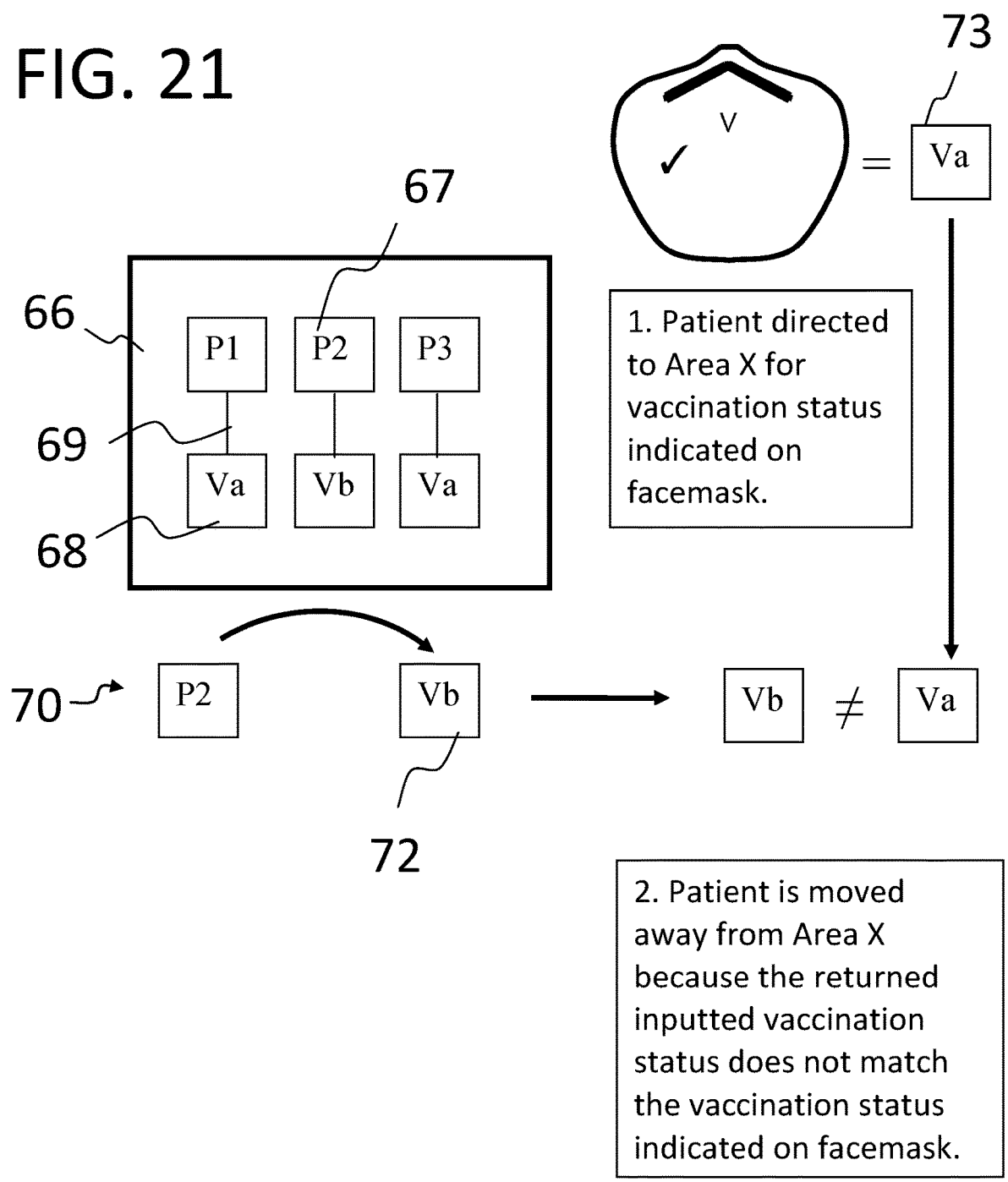

PATIENT FACE MASK FOR IDENTIFYING VACCINATION STATUS AND CONTROLLING MOVEMENT WITHIN A MEDICAL FACILITY

CROSS-REFERENCE TO RELATED APPLICATIONS

This application claims the benefit of U.S. Provisional Patent Application No. 63/207,696, entitled, "Smart Mask," filed on Mar. 16, 2021, the content of which is hereby incorporated by reference herein in its entirety.

BACKGROUND OF THE INVENTION

(1) Field of the Invention

The present disclosure relates to a face mask which displays information. Particularly the disclosure relates to a face mask which displays information related to the person wearing the face mask. Additionally, the information displayed can relate to the vaccination status of the wearer of the face mask.

(2) Description of Related Art Including Information Disclosed Under 37 CFR 1.97 and 1.98

Face masks are worn to prevent the spread of respiratory diseases such as COVID-19, influenza, meningitis, and other diseases. A face mask can be worn to protect the person wearing the face mask. Also, a face mask can be worn to protect people near the person wearing the face mask.

During outbreaks of widespread diseases, such as COVID-19, a majority of the population may wear a face mask when people are near each other. During an outbreak of a disease, a portion of the population may be receiving preventative treatment for the disease. The type of preventative treatment such as a vaccine, and the level of completion of the preventative treatment regime can change the likelihood of the transmission of the disease, from the person who received the preventative treatment to another person.

BRIEF SUMMARY OF THE INVENTION

The following disclosure relates to a face mask which displays information about the vaccination status of the wearer of the face mask. In addition, other medical information could be displayed on the mask. The face mask can also be used to move people to an area designated for people with the same vaccination status.

The information is prominently displayed so others can view the information from a distance and in low visibility situations.

The information is displayed in a standardized way so others do not have to ask the wearer about the information displayed on the face mask.

BRIEF DESCRIPTION OF THE SEVERAL VIEWS OF THE DRAWING(S)

FIG. 1 is a front view of an embodiment of a face mask

Figure 2:
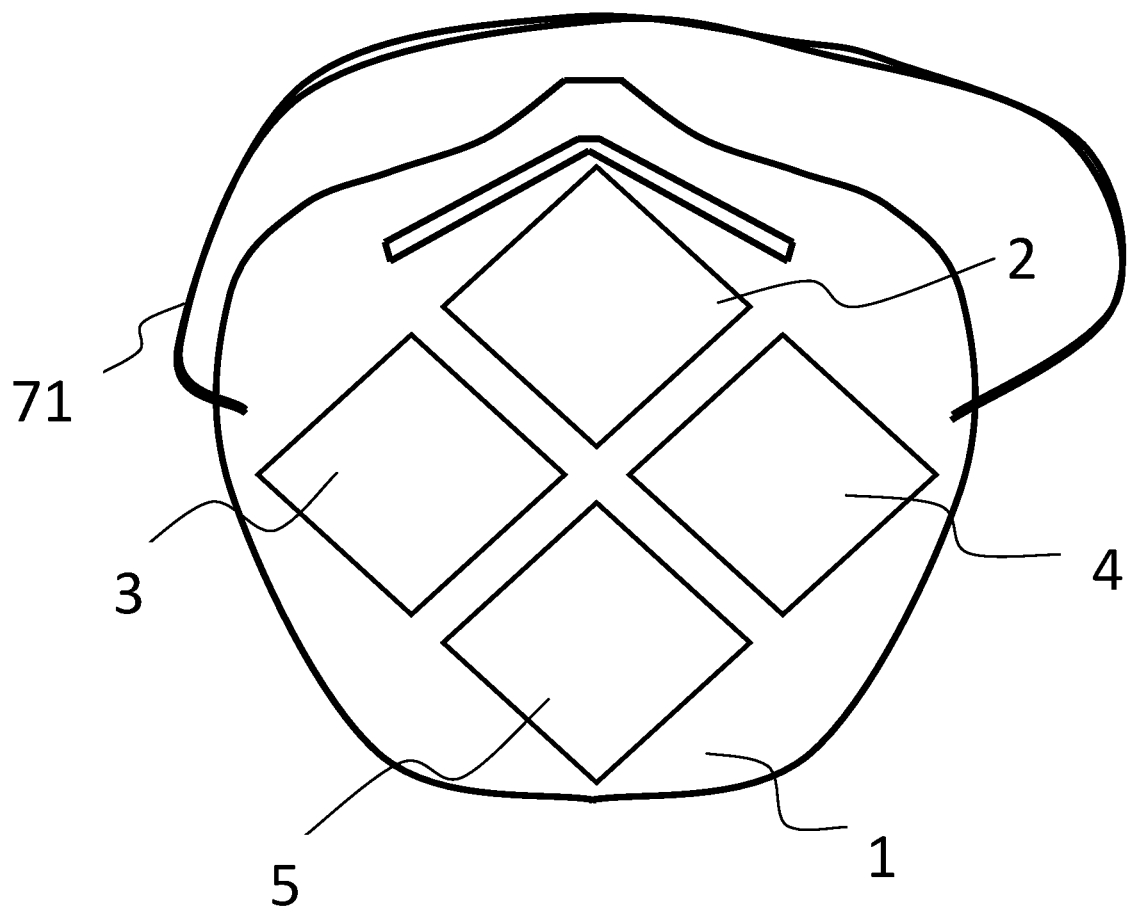
Figure 3:
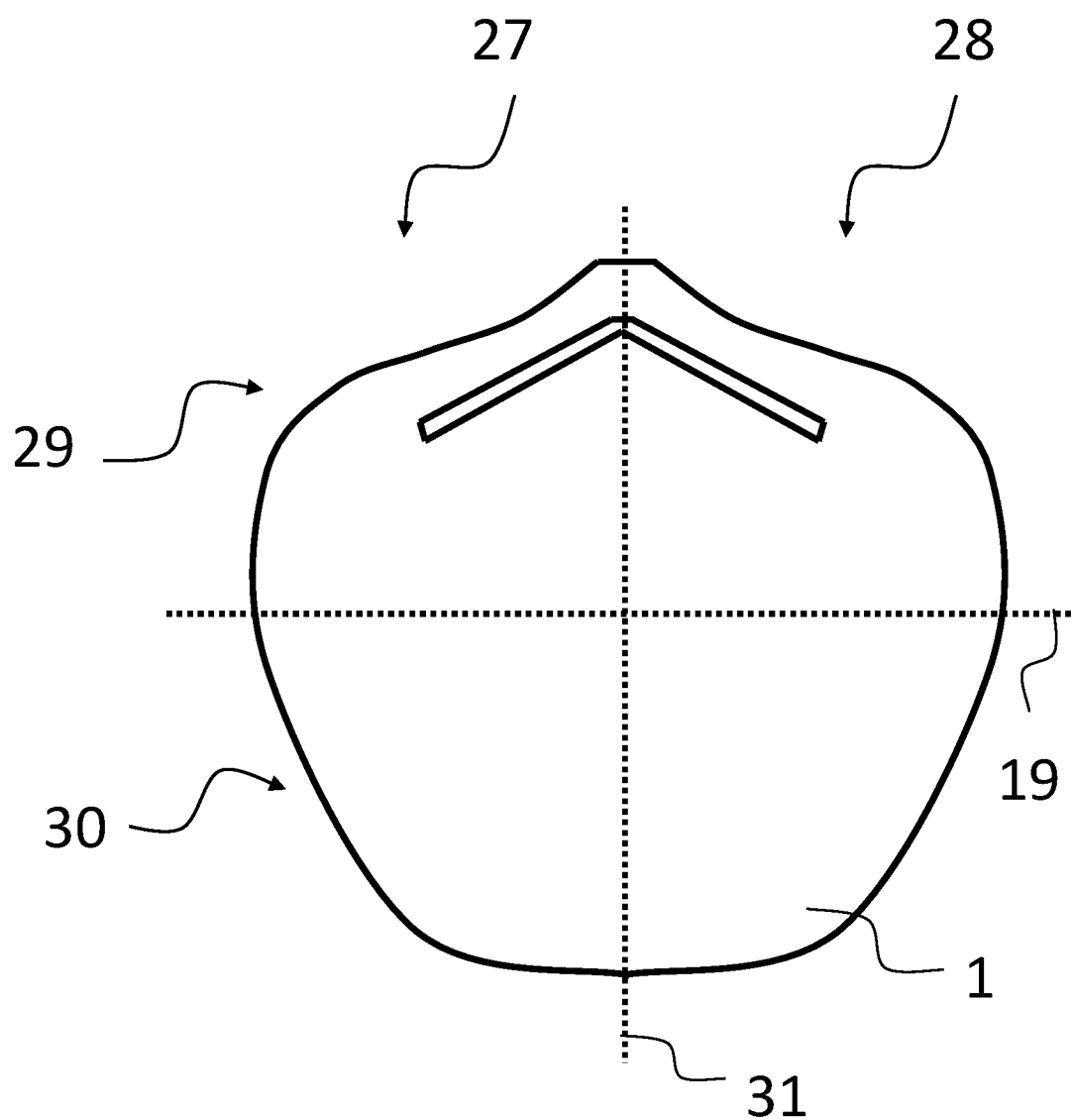
Figure 4:
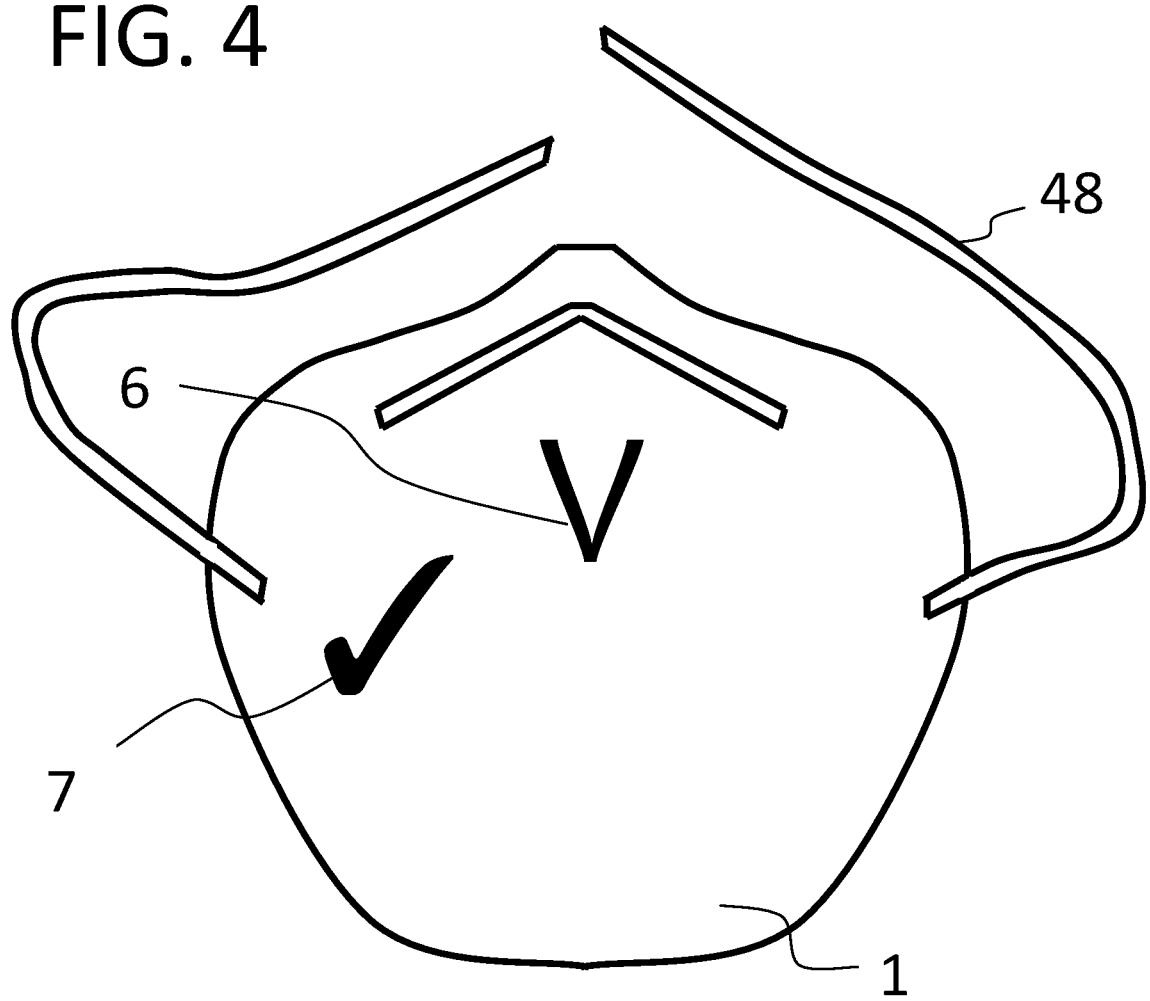
Figure 5:
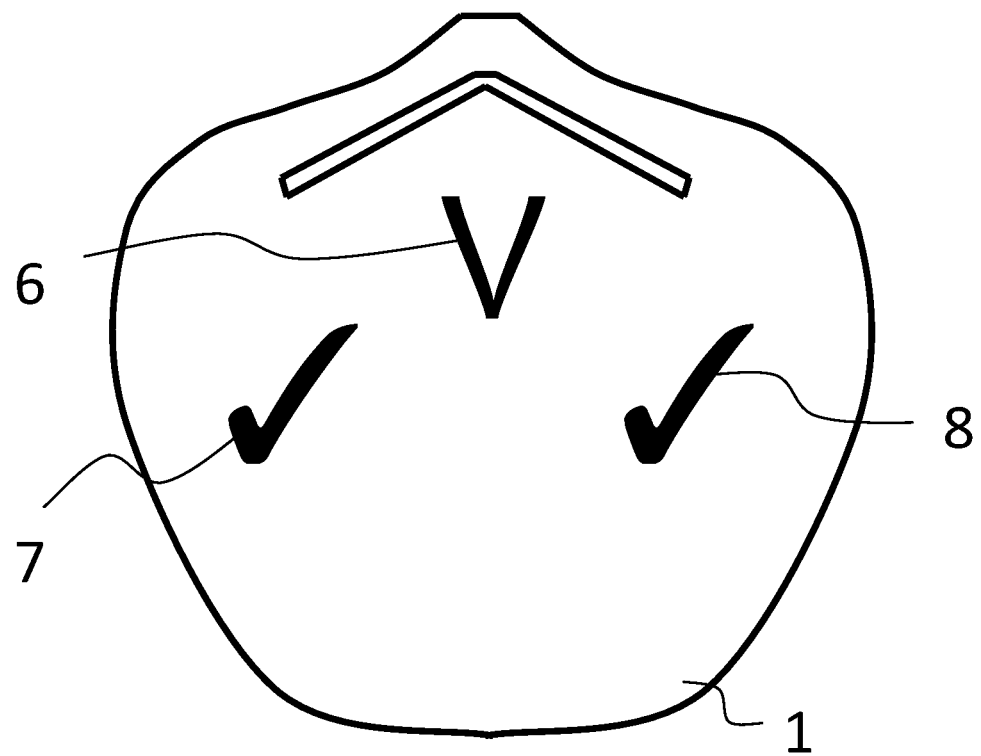
Figure 6:
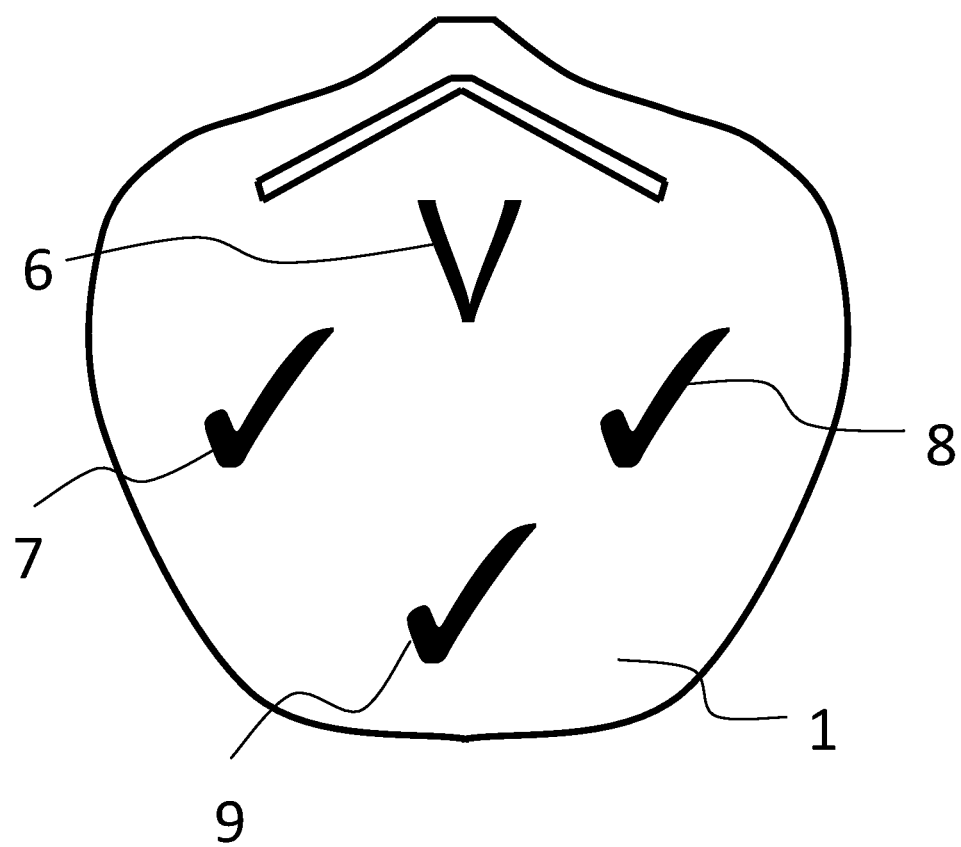
Figure 7:
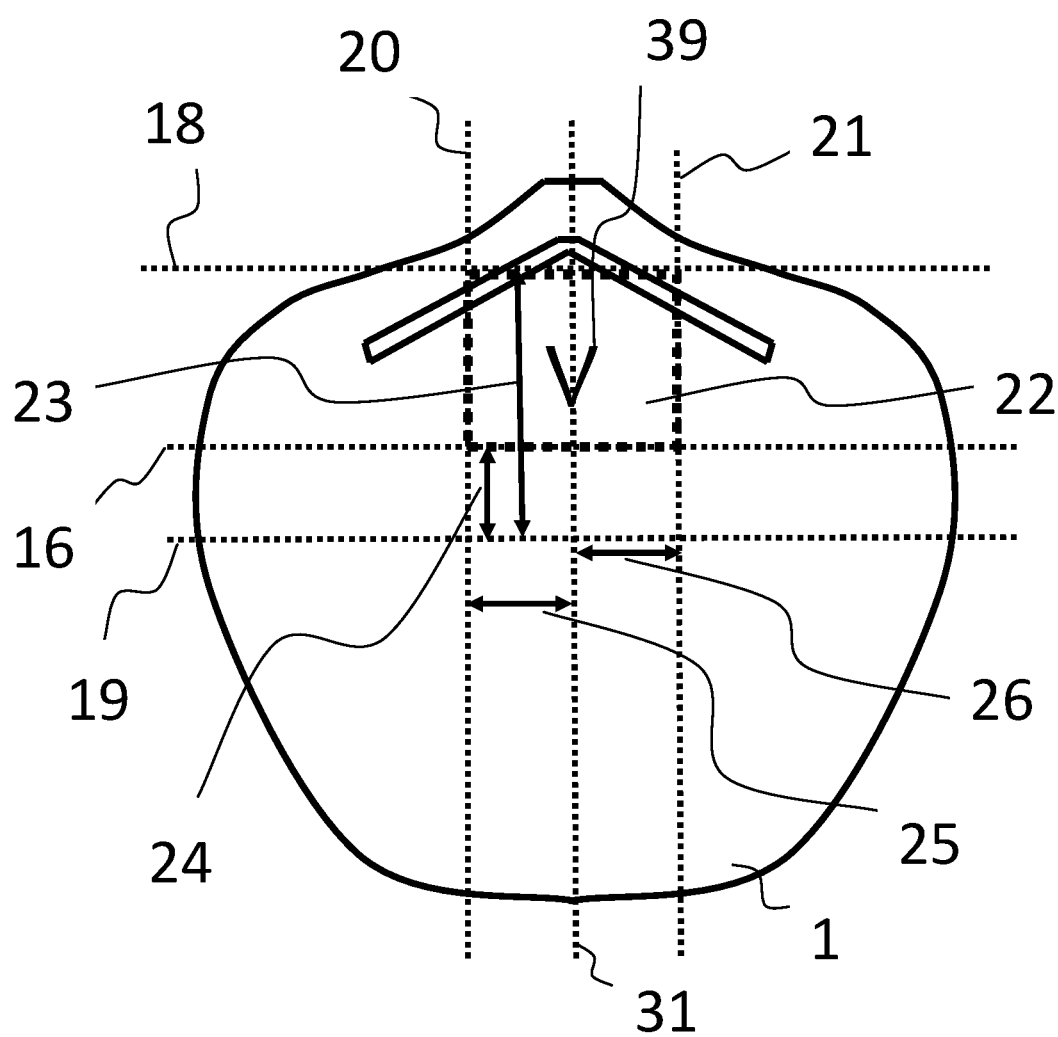
Figure 8:
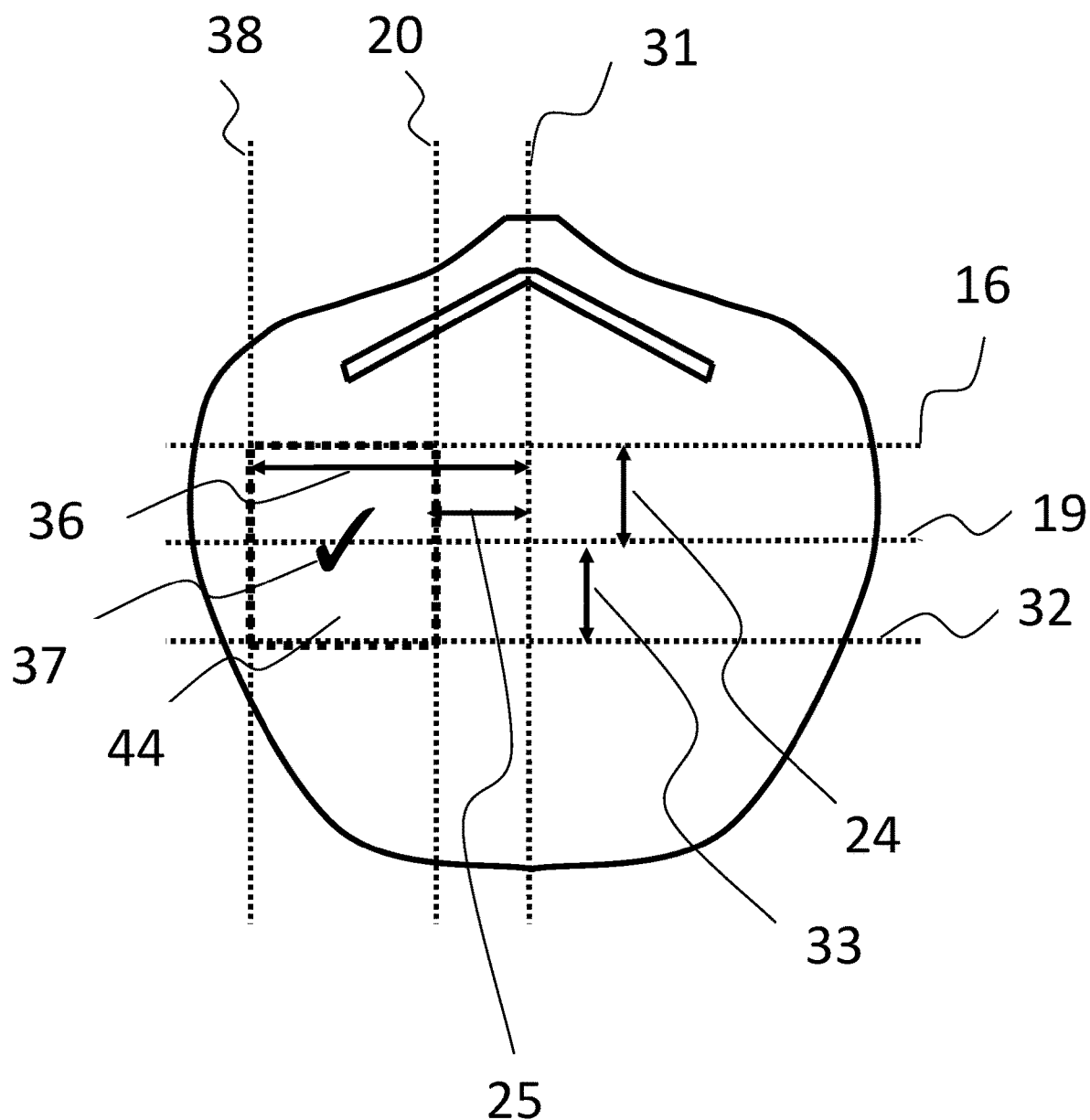
Figure 9:
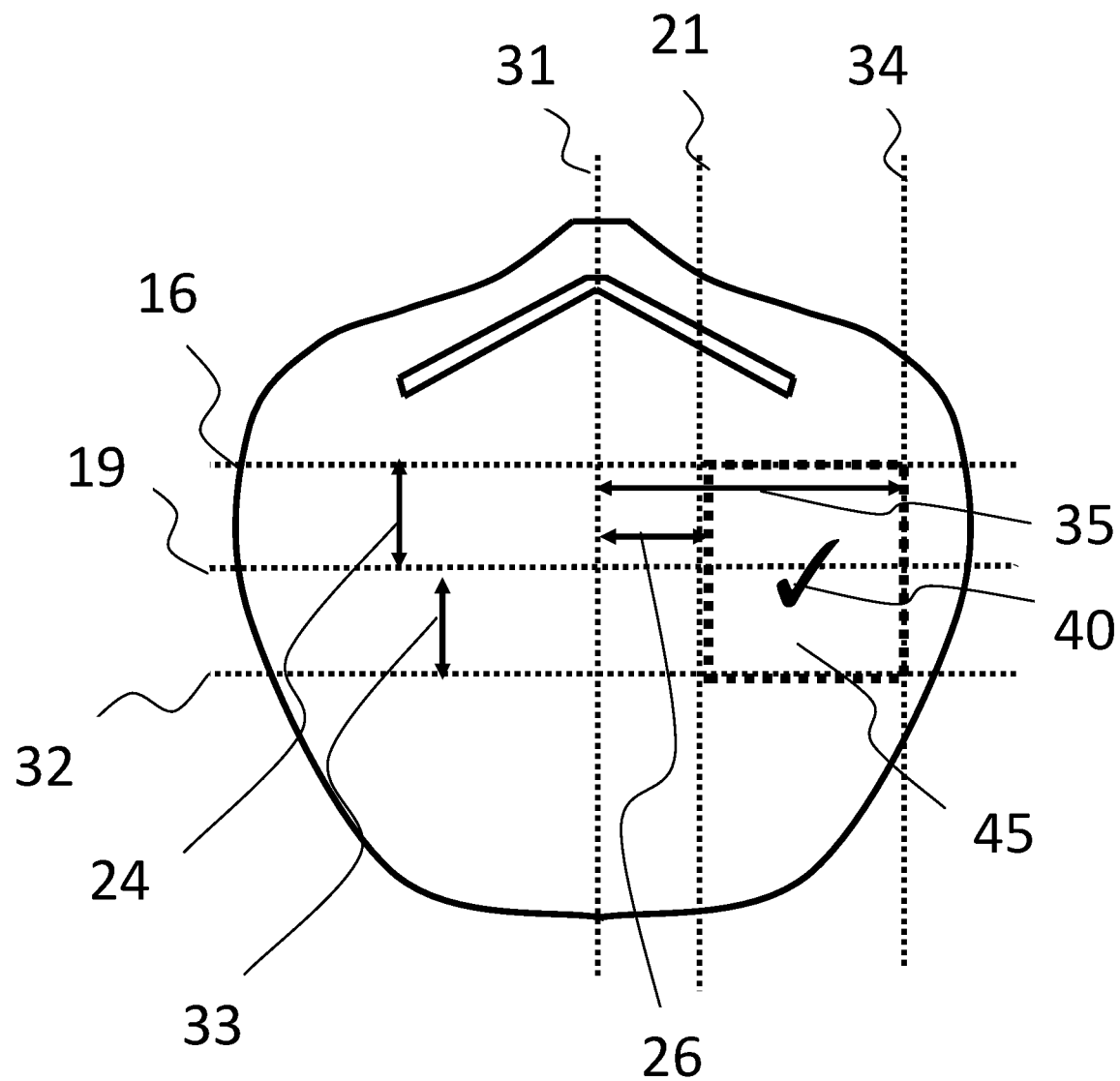
Figure 10:
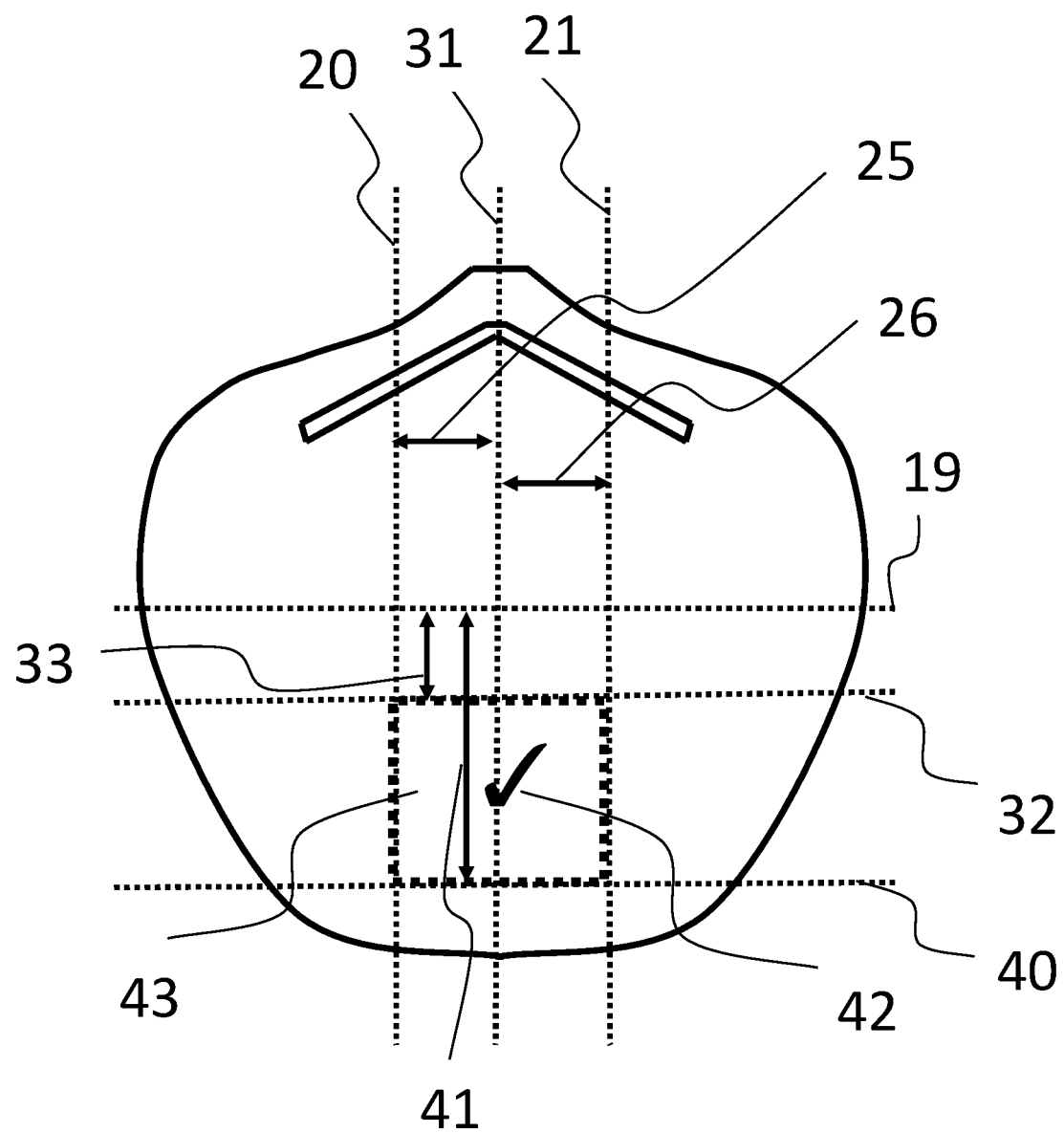
Figure 11:
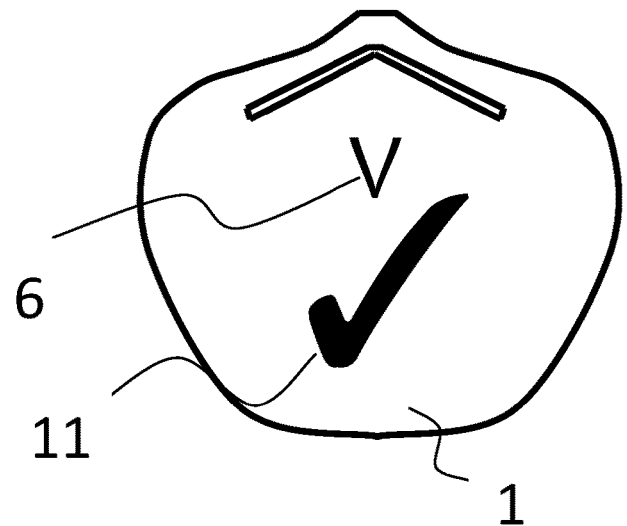
Figure 12:
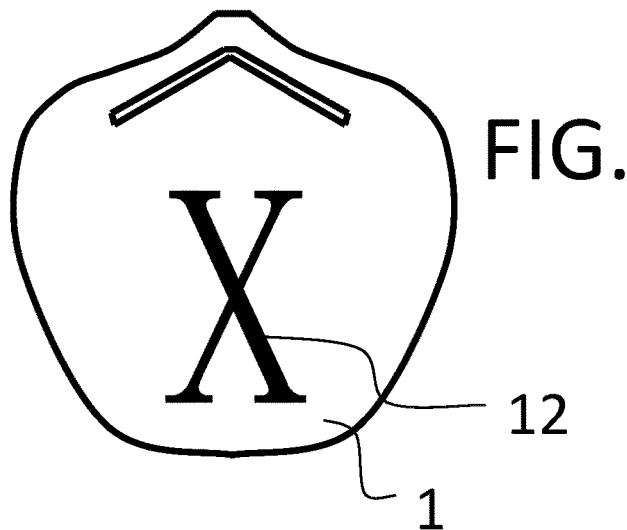
Figure 13:
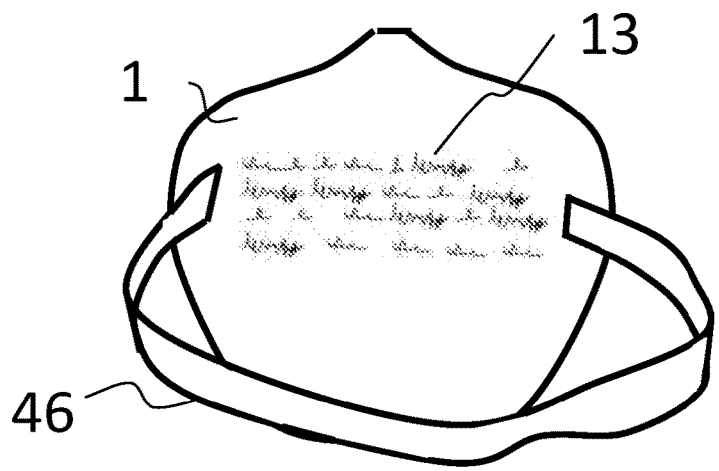
Figure 14:
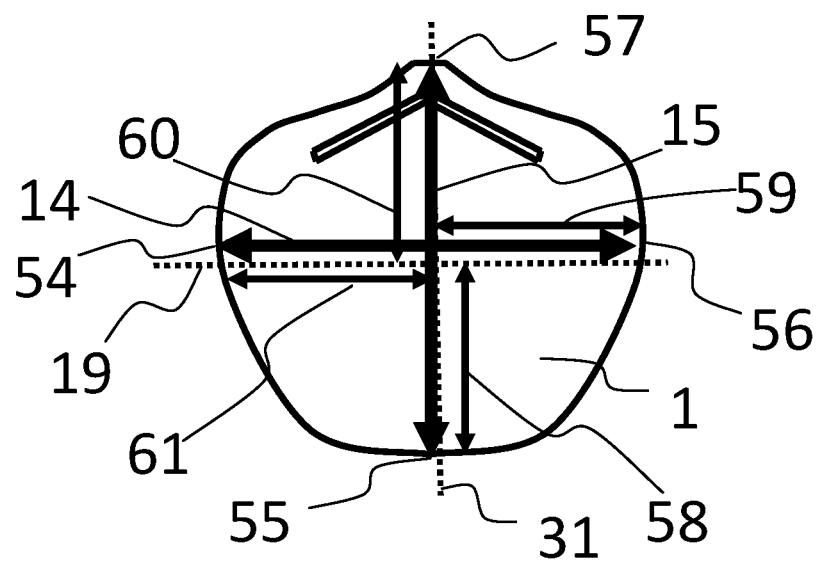
Figure 15:
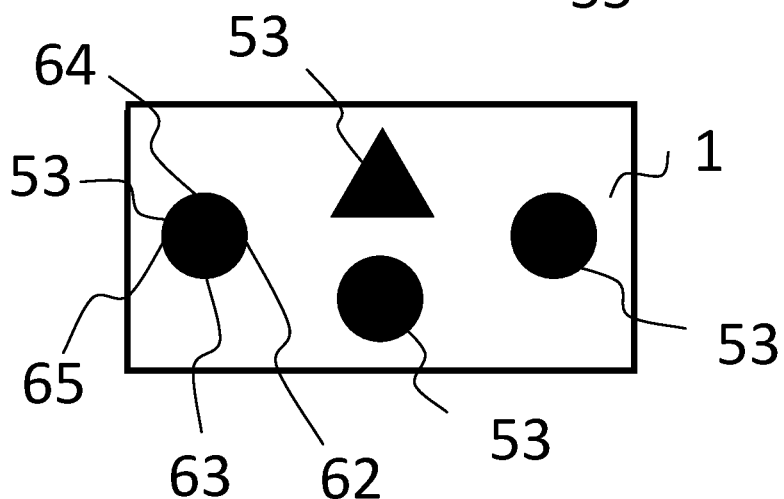
Figure 16:
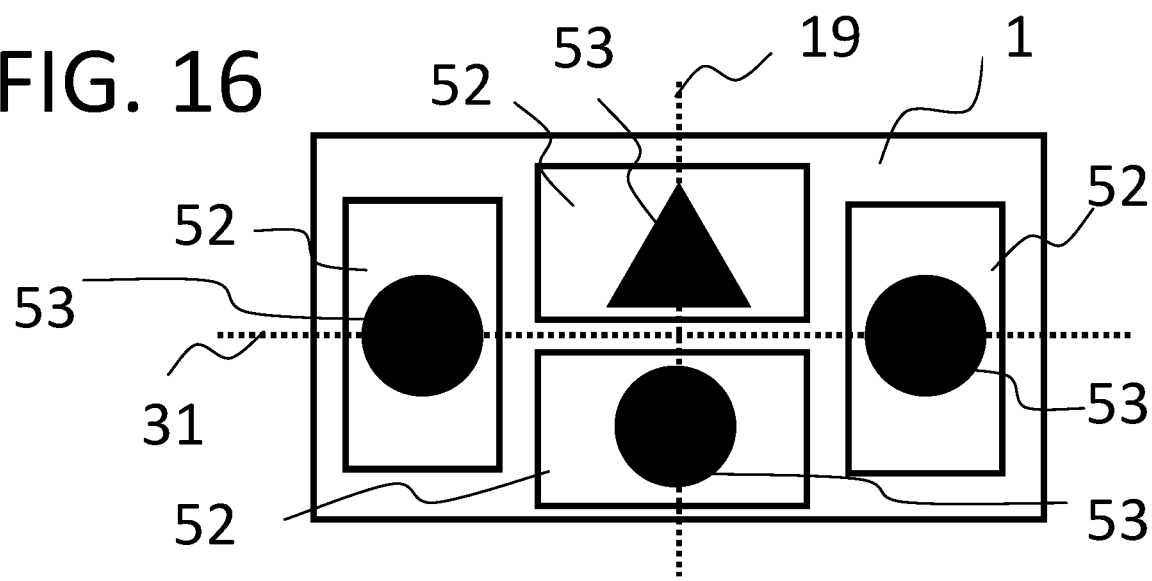
Figure 17:
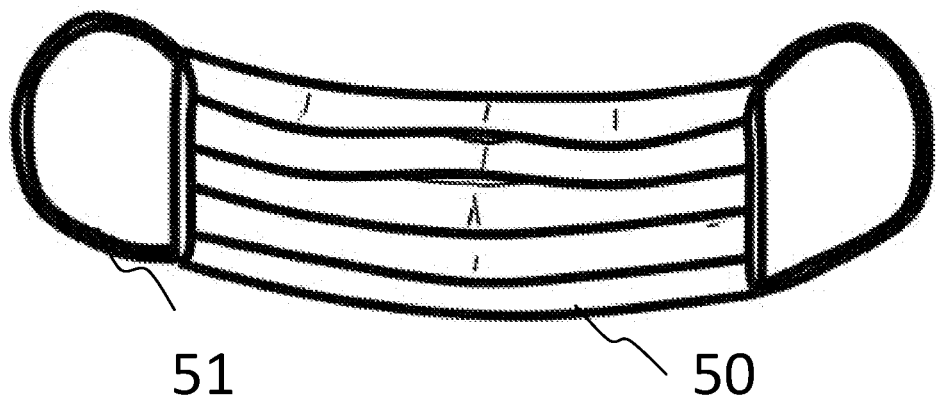
Figure 18:
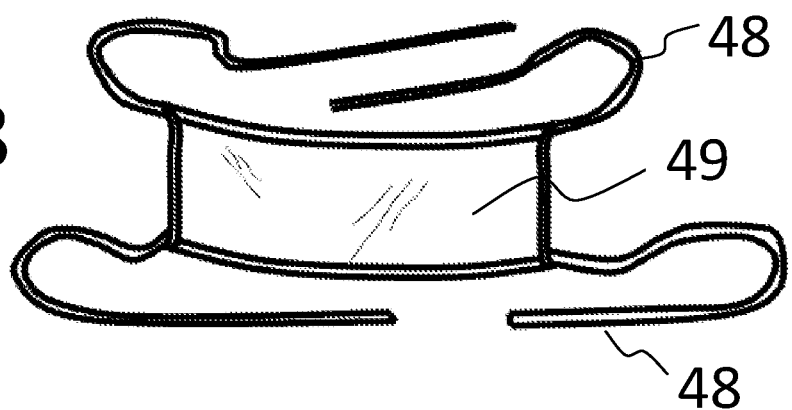
Figure 19:
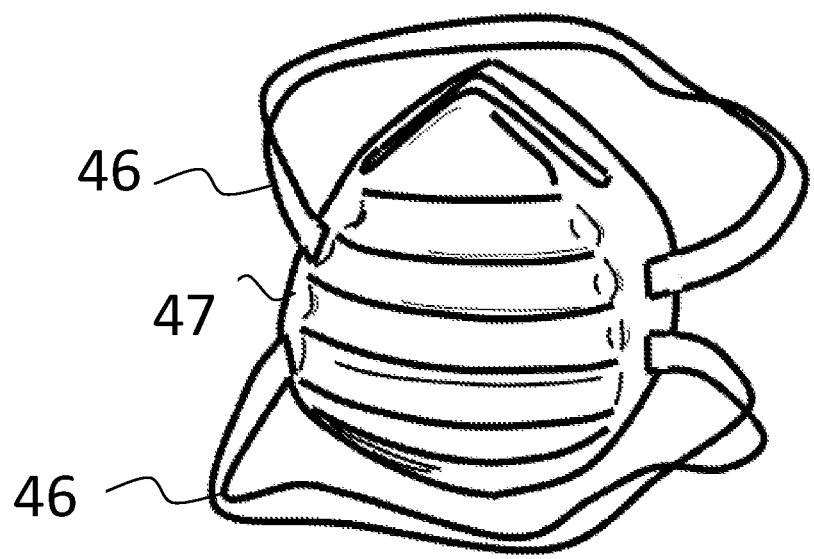

FIG. 2 is a front view of an embodiment a face mask with a face covering structure with marking areas defined by continuous lines on the top, left, right, and bottom on the outer surface of the face covering structure FIG. 3 is a front view of an embodiment of a face covering structure with a representation of the axis dividing the top and bottom area and the axis dividing the left and right area of the face covering structure FIG. 4 is a front view of an embodiment of a face mask with a face covering structure with markings on the top and left area on the outer surface of the face covering structure FIG. 5 is a front view of an embodiment of a face covering structure with markings on the top, left, and right area on the outer surface of the face covering structure FIG. 6 is a front view of an embodiment of a face covering structure with markings on the top, left, right, and bottom area on the outer surface of the face covering structure FIG. 7 is a front view of an embodiment of a face covering structure with a marking on the top area on the outer surface of the face covering structure, within a defined marking area, based on ratios of the distance from the axis dividing the top, bottom, left, and right areas, and the topmost, bottommost, leftmost, and rightmost part of the face covering structure FIG. 8 is a front view of an embodiment of a face covering structure with a marking on the left area on the outer surface of the face covering structure, within a defined marking area, based on ratios of the distance from the axis dividing the top, bottom, left, and right areas, and the topmost, bottommost, leftmost, and rightmost part of the face covering structure FIG. 9 is a front view of an embodiment of a face covering structure with a marking on the right area on the outer surface of the face covering structure, within a defined marking area, based on ratios of the distance from the axis dividing the top, bottom, left, and right areas, and the topmost, bottommost, leftmost, and rightmost part of the face covering structure FIG. 10 is a front view of an embodiment of a face covering structure with a marking on the bottom area on the outer surface of the face covering structure, within a defined marking area, based on ratios of the distance from the axis dividing the top, bottom, left, and right areas, and the topmost, bottommost, leftmost, and rightmost part of the face covering structure FIG. 11 is a front view of an embodiment of a face covering structure with a marking on the top area of the face covering structure on the outer surface of the face covering structure and a check mark on the outer surface of the face covering structure FIG. 12 is a front view of an embodiment of a face covering structure with a single letter X on the outer surface of the face covering structure FIG. 13 is a rear view of an embodiment of a face covering structure with detailed information on the inner surface of the face covering structure FIG. 14 is a front view of an embodiment of a face covering structure showing the height and width of the face covering structure and other measurements to the outermost parts of the face covering structure on the top, bottom, right and left from the top-bottom and left-right axis FIG. 15 is a front view of an embodiment of a face covering structure showing markings which cover at least a certain percentage of the surface area of the outer surface of the face covering structure FIG. 16 is a front view of an embodiment of a face covering structure showing marking areas defined by continuous lines, and markings, where both the marking areas and markings cover at least a certain percentage of the surface area of the outer surface of the face covering structure FIG. 17 is a front view of an embodiment of a face mask with a face covering structure of a pleated paper rectangle and a face covering securing structure of ear loops FIG. 18 is a front view of an embodiment of a face mask with a face covering structure of a fabric rectangle and a face covering securing structure of ties FIG. 19 is a front view of an embodiment of a face mask with a face covering structure of a flexible molded dome and a face covering securing structure of straps FIG. 20 is a description of the steps of moving a patient wearing a face mask indicating their vaccination status to the appropriate location of a medical facility based on the vaccination status indicated on the face mask, then checking the vaccination status of the patient from information in a database, and then moving the patient if the vaccination status from the face mask and database does not match FIG. 21 is a depiction of the database holding patient identities and inputted vaccination statuses, and the entering of a patient identity resulting in an returned inputted vaccination status available, and moving a patient from one area to another based on the facemask and database information not matching

DETAILED DESCRIPTION OF THE INVENTION

At different times it is important for individuals to have information about one another. There can be a benefit of making that information readily available to other people. This is true for situations such as a pandemic where people in the community want to know if others have been vaccinated for the disease causing the pandemic.

People may want to know whether another person has been vaccinated. Information about whether a person has been vaccinated can be broken down into further information about the complete information about another person's vaccination status. Other times medical professionals may want to know urgent information as to whether a patient was vaccinated for the pandemic-causing disease when treating the patient. Additionally, if the vaccination status can be conveyed when the person is not conscious such as in an emergency medical situation, that is a valuable advantage.

A vaccine is a general term for a medical treatment which is meant to prevent a patient from developing an infectious disease, or reduce the severity of an infectious disease if infected. A vaccine can be administered by a vaccine inoculation, of an injection into the body of the patient with a needle and syringe. Some vaccines require one dose of a vaccine inoculation. Some vaccines require two doses of a vaccine inoculation. Some vaccines require three doses of a vaccine inoculation. For a vaccine requiring three doses of a vaccine inoculation, the inoculations can be called, dose 1, dose 2, and a booster. The single vaccine inoculation or the multiple vaccine inoculations can be called a vaccine regime, where the single inoculation or the multiple inoculations are a preset treatment step or steps which are the regime. A regime is a term to describe the defined steps and actions for a medical treatment, such as a complete vaccine administration. A regime can be a single event or multiple events over time such as months.

The term vaccination status is used to describe information about receiving a vaccine. Vaccination status can include information about if any doses of the vaccine were received and how many doses of the vaccine inoculation were received. This information will indicate the completeness of a regime to fully vaccinate a patient.

The ability to transfer information about someone's vaccination status at a distance is helpful. Since the information is related to a contagious disease, the ability to inform others at a distance is an added advantage because the disease is more likely to be transmitted from one person to another, when people are physically close to one another. Also shouting or yelling with a contagious respiratory virus can potentially lead to more spreading of the disease. Therefore, having the information visible from a distance is helpful. Also the maximum visibility is also important because during a pandemic many people wear face masks 16 which frequently cause their eyeglasses to fog-up and decrease visual acuity.

When a face mask 16 is worn by one person, the face mask 16 is very visible to another person. The face of a person is the focal point of attention to another person. Additionally, commonly there is nothing which will cover or obstruct the viewing of the face mask 16 because normally the front of a person's face is unobstructed. Only in special circumstances, such as a pandemic is the face covered. Since the face is usually exposed, there normally is nothing which will be worn over a face mask 16. Also the combination of the information of a wearer's vaccination status and the face mask 16 requires less work by the wearer because the face mask 16 is being worn to prevent the spread of the infectious disease, therefore it is one less step for the wearer to indicate their vaccination status to others with another article worn on the body like a headband, pin, or other object. Therefore, a face mask 16 is a very useful place to transmit the information related to vaccination status to others.

A face mask 16 can also be called a respirator mask.

Embodiments of the face mask 16 can be of multiple styles and materials. The portion of the face mask 16 which covers the face is the face covering structure 1 47 50 49. The face covering structure 1 can be: a dome 1 47; pleated paper 50; fabric 49; or a molded material with added filters. The face covering structure 1 is held in place on the wearer of the face mask 16 by a face covering securing structure 17, 51, 48, 46, 71 which can be: ear loops 51; a single loop 71 or loops around the head and neck; tie 48 or ties which can be tied behind the head and neck; a band 17, or a strap 46 or straps. A loop 71 is usually thinner than a band 17, which is thinner than a strap 46. A strap face covering securing structure 46 can have buckles or no buckles for adjustment. The face covering securing structures 17, 51, 48, 46, 71 can be made of: elastic, plastic, rubber, fabric, or string.

The face covering structure 1 has an outer surface and an inner surface.

The information about the vaccination status of the wearer is displayed on the outer surface of the face covering structure 1. The information about the vaccination status of the wearer is displayed in such a way as to make the information visible to another person at a distance and when the vision of the other person may be impaired. The impairment of vision is frequent when the other person's eyeglasses fog-up when also wearing a face mask 16.

An embodiment of the face mask 16 is shown in FIG. 1. The face covering structure 1 in FIG. 1 is a semi-rigid cup form style. Semi-rigid can also be called flexible. The cup form can also be called a dome shape or molded dome. The cup form does not need to be symmetrical in all dimensions like part of a sphere. The cup form can have some irregularities, away from perfect symmetry in its shape, to fit over a human face, allowing for a tight fit. Also, the irregularities, away from perfect symmetry in its shape, can allow for an optimal distance of the material of the cup to extend away from the wearer's face allowing for enough distance between the face and the material of the face covering structure 1 and not too far of an extension causing problems of being cumbersome to wear. With a cup form style face covering structure 1, the outer rim of the face covering structure 1 touches the wearer's face. The point of contact between the wearer's face and the face covering structure 1 is in a line which goes from the bridge of the nose, over a cheek, near the jaw, to the chin and back near the jaw on the other side of the wearer's face, then the other cheek and the other side of the wearer's bridge of the nose.

In FIG. 2 is an embodiment of the face covering structure 1 with four marking areas 2, 3, 4, 5 indicated on the face covering structure 1 where markings related to the wearer's vaccination status can be placed. The outer surface of the face covering structure 1 is shown in FIG. 2. The four marking areas can be further defined as the top marking area 2, the left marking area 3, the right marking area 4, and the bottom marking area 5. The marking areas in FIG. 2 are defined by continuous lines on the surface of the face covering structure 1.

A marking area is a part of the outer surface of the face covering structure 1. A marking area can be defined as top, left, right, or bottom. A marking area can be defined by lines on the surface of the face covering structure 1. A continuous line for a marking area is a line which does not have a break in the line defining the marking area. The continuous line can hit another line which does not make up the continuous line surrounding the marking area.

Other marking areas may not have lines on the surface of the face covering structure 1, which define the marking area.

A marking area is defined by the area of the outer surface of the face covering structure 1 where the marking area is located. The top area 29 of the face covering structure 1 is the area above the top-bottom axis 19. The top-bottom axis is equal distant from the topmost part 57 and the bottommost part 55 of the face covering structure 1. The bottom area 30 of the face covering structure 1 is the area below the top-bottom axis 19. The left area 27 of the face covering structure 1 is the area to the left of the left-right axis 31, with a front view of the outer surface of the face covering structure 1 with the top of the face covering structure 1 on top. The left-right axis 31 is equal distant from the leftmost part 54 and the rightmost part 56 of the face covering structure 1. The right area 28 of the face covering structure 1 is the area to the right of the left-right axis 31, with a front view of the outer surface of the face covering structure 1 with the top of the face covering structure 1 on top. The top of the face covering structure 1 is defined by the part which when worn will be closer to the top of the person's head and not the part closer to the person's chin. A top marking area is on the top area 29. A bottom marking area is on the bottom area 30. A left marking area is on the left area 27. A right marking area is on the right area 28.

The top 29, left 27, right 28, and bottom 30 areas can be also called quadrants and respectively top, left, right and bottom quadrants.

A marking is defined as in the top area 29 of the face covering structure 1 if the marking is in the top area 29 of the face covering structure 1, as defined with the top-bottom axis 19. A marking defined as in the top area 29 of the face covering structure 1, will not have any part of the marking in the bottom area 30 of the face covering structure 1. A marking defined in the top area 29 of the face covering structure 1, will have a portion of the marking in the left area 27 and right 28 area of the face covering structure 1, as defined with the left-right axis 31.

A marking is defined as in the bottom area 30 of the face covering structure 1 if the marking is in the bottom area 30 of the face covering structure 1 as defined with the top-bottom axis 19. A marking defined as in the bottom area 30 of the face covering structure 1, will not have any part of the marking in the top area 29 of the face covering structure 1. A marking defined in the bottom area 30 of the face covering structure 1, will have a portion of the marking in the left area 27 and right area 28 of the face covering structure 1, as defined with the left-right axis 31.

A marking is defined as in the left area 27 of the face covering structure 1 if the marking is in the left area 27 of the face covering structure 1 as defined with the left-right axis 31. A marking defined as in the left area 27 of the face covering structure 1, will not have any part of the marking in the right area 28 of the face covering structure 1. A marking defined in the left area 27 of the face covering structure 1, will have a portion of the marking in the top area 29 and bottom area 30 of the face covering structure 1, as defined with the top-bottom axis 19.

A marking is defined as in the right area 28 of the face covering structure 1 if the marking is in the right area 28 of the face covering structure 1 as defined with the left-right axis 31. A marking defined as in the right area 28 of the face covering structure 1, will not have any part of the marking in the left area 27 of the face covering structure 1. A marking defined in the right area 28 of the face covering structure 1, will have a portion of the marking in the top area 29 and bottom area 30 of the face covering structure 1, as defined with the top-bottom axis 19.

In each of the marking areas there can be one or more: letters, symbols, numbers, or indicia. In certain embodiments some marking areas can be left blank with no letter, symbol, or number. In other embodiments each of the marking areas will have at least one letter, symbol, or number.

A marking is a symbol 7, letter 6, letters or other indicia 53 which is visible on the surface on the outer surface of the face covering structure 1. A marking be a single symbol 7, letter 6, or other indicia 53. Or, a marking can be a combined set of more than one symbol 7, letter 6, or other indicia 53. A combined set is defined where the individual indicia are closer to each other than any other indicia on the outer surface of the face covering structure 1, and individual indicia which are part of the combined set, to make up the whole marking, are all in the same area of the outer surface of the face covering structure 1, so all in the top 29, left 27, right 28, or bottom 30, when the whole combined set is considered one marking. An example would be the letters Bn on the top area 29, a check mark on the left area 27, and a check mark in the right area. The letters of B and n, or individual indicia, would be a combined set, where both together would be the marking. The B and the n are closer to each other than to any other marking on the outer surface of the face covering structure 1. Also when combined together, no part of the B or n would be in the bottom area 30, and part of the combined set would be in the left area 27 and part of the combined set would be in the right area 28.

The wording of describing a marking as "on" or "in" an area, is considered equivalent.

The marking on the surface can be: ink printed on the surface; paint on the surface; embroidery with thread on the surface; or a cut out of material with one material stacked on each other with each material a different color where the cut out gives the shape and contrast in color for the marking. Different embodiments of the face covering structure 1 can have different combinations of letters or symbols as the markings on the outer surface of the face covering structure 1. A letter, as defined for a marking, is a capital or lower case letter of A-Z of the standard English alphabet.

In FIGS. 4, 5, and 6 other embodiments of the face covering structure 1 are shown. In FIGS. 4, 5, and 6 the four marking areas are not marked with lines on the face covering structure 1. Without the four marking areas indicated with lines a marking area will be the top 29, left 27, right 28, and/or bottom area 30 of the face covering structure 1. As in FIG. 3, the top area 29 and bottom area 30 of the face covering structure 1 are separated by a top-bottom axis 19. The top-bottom axis 19 can also be called the axis dividing the top and bottom area of the face covering structure 1. The left area 27 and right area 28 of the face covering structure 1 are separated by a left-right axis 31. The left-right axis 31 can also be called the axis dividing the right and left area of the face covering structure 1.

The top of the face covering structure 1 is determined by the form of the face covering structure 1, where the face mask 16 can have a specific molding to fit over the bridge of the nose for face covering structures 1, for embodiments such as molded domes 47, or a wire to compress and fit over the bridge of the nose for face covering structures 1 for embodiments such as pleaded paper 50. The part of the face covering structure 1 which fits over the bridge of the nose in the top of the face covering structure 1. If the face covering structure 1 does not have a structural indication for the top, then the top will be assigned where the top is the marking area which will give the first piece of the information about the wearer's vaccination status. The first piece of information indicated in a marking area will be on the top 29, then the left 27, then the right 28, and last the bottom 30 area for markings areas not defined by lines or with lines. If the face covering structure 1 does not have a structural indication for the top and there are markings in all four areas of top 29, left 27, right 28, and bottom area 30, then the marking in the top area will be the one marking which is different from the remaining other three markings and the other three markings will be the same.

In FIG. 4, an embodiment of the face covering structure 1 has a marking of a letter 6 on the top area 29 and a marking of a symbol of a check mark 7 on the left area 27. The outer surface of the face covering structure 1 is shown in FIG. 4.

In FIG. 5 there is an embodiment of the face covering structure 1 with a marking of a letter 6 on the top area 29 and a marking of a symbol of a check mark 7 on the left area 27 and on the right area 28. The outer surface of the face covering structure 1 is shown in FIG. 5.

In FIG. 6 is an embodiment of the face covering structure 1 with a marking of a letter 6 on the top area 29 and a marking of a symbol of a check mark 7 on the left area 27, right area 28, and bottom area 30. The outer surface of the face covering structure 1 is shown in FIG. 6.

The arrangement of markings allow for different information to be conveyed. The different embodiments in FIGS. 4, 5, and 6, allow for a particular meaning of the vaccination status of the wearer of the mask.

The embodiment in FIG. 4 with a face covering structure 1 with a marking of a letter 6 in the top area 29 and a marking of a symbol of a check mark 7 in the left area 27, allows for the display of the vaccination status of the first dose of a vaccine regime. The check mark 7 on the left area 27 can indicate that the wearer received the first dose of the vaccine regime. The letter on the top area 29 can indicate the vaccine regime is from a vaccine maker which is defined by the abbreviation of the vaccine maker.

The embodiment in FIG. 5 with a face covering structure 1 with a marking of a letter 6 in the top area 29 and a marking of a symbol of a check mark 7 in the left area 27 and right area 28, allows for the display of the vaccination status of the first dose and second dose of a vaccine regime received. The check mark 7 on the left area 27 can indicate that the wearer received the first dose of the vaccine regime. The check mark 7 on the right area 28 can indicate that the wearer received the second dose of the vaccine regime. The letter on the top area 29 can indicate the vaccine regime is from a vaccine maker which is defined by the abbreviation of the vaccine maker.

The embodiment in FIG. 6 with a face covering structure 1 with a marking of a letter 6 in the top area 29 and a marking of a symbol of a check mark 7 in the left area 27, right area 28, and bottom area 30, allows for the display of the vaccination status of the first dose, second dose, and booster dose of a vaccine regime received. The check mark 7 on the left area 27 can indicate that the wearer received the first dose of the vaccine regime. The check mark 7 on the right area 28 can indicate that the wearer received the second dose of the vaccine regime. The check mark 7 on the bottom area 30 can indicate that the wearer received a booster dose of the vaccine regime. A booster dose means that an extra dose of the vaccine was given past the initial vaccine regime of two doses. The letter on the top area 29 can indicate the vaccine regime is from a vaccine maker which is defined by the abbreviation of the vaccine maker.

In FIG. 11 is an embodiment of a face covering structure 1 with a marking of a letter 6 on the top 29 area. Also, there is a symbol of a check mark 7 which cannot be defined as the a marking as in the other embodiments because the check mark 7 falls in a portion of the top 29, left 27, right 28, and bottom 30 area. The outer surface of the face covering structure 1 is shown in FIG. 11. The embodiment in FIG. 11 can indicate the vaccination status of the wearer. The check mark 7 can indicate that all the doses required for a normal regime were received, which would indicate the vaccination status of fully vaccinated. The letter on the top area 29 can indicate the vaccine regime is from a vaccine maker which is defined by the abbreviation of the vaccine maker's name as a letter.

The embodiment in FIG. 12 of a face covering structure 1 with a letter of an X 12 large enough to fall in the top 29, left 27, right 28, and bottom 30 area. The letter 12 cannot be defined as a marking as in the other embodiments because the letter 12 falls in a portion of the top 29, left 27, right 28, and bottom 30 area. The embodiment in FIG. 12 can indicate that all the doses required for a normal regime were received, which would indicate the vaccination status of fully vaccinated.

In FIG. 13 is an embodiment of a face covering structure 1 showing the inner surface of the face covering structure 1, where more detailed information 13 is on the inner surface of the face covering structure 1. The detailed information 13 can include medical information about the wearer. The detailed information 13 can also include information about the markings of letters, symbols, or numbers on the outer surface of the face covering structure 1.

FIG. 16 shows a rectangular face covering structure 1 with markings areas defined by continuous lines, where a surface area of at least 10 percent of the surface area of the face covering structure 1 is enclosed by the marking areas 52. The surface area which the marking area encloses does not include the area of the continuous line itself defining the marking area. The surface area enclosed by of the marking area is the area enclosed by the continuous line, not the actual line. Only continuous lines can enclose a marking area where a measured percentage of surface area is enclosed. Also in FIG. 16, at least 5 percent of the surface area of the face covering structure 1 is covered by each of the markings 53. The surface area a marking covers is only the colored element of the marking which is different from the outer surface of the face covering structure 1. For example, if a marking is an indicia that is line forming the outline of the indicia, then the surface area of the line is the basis for measuring a percentage of surface area covered. Only markings which are a solid color with clear edges, not a fuzzy indicia, can be measured as a percentage of surface area covered.

FIG. 15 shows a rectangular face covering structure 1 where at least 5 percent of the surface area of the face covering structure 1 is covered by each of the markings 53.

In FIG. 14 is a front view of the outer surface of an embodiment of a face covering structure 1. The double headed arrow 14 shows the left to right width of the face covering structure 1. The double headed arrow 15 shows the top to bottom height of the face covering structure 1. Typically the width of a face covering structure 1 is approximately 5 inches, based on the typical size of a human face. Typically the height of a face covering structure 1 is approximately 5 inches, based on the typical size of a human face. The face covering structure 1 can range from 4.5 to 6.5 inches from top to bottom and 4.5 to 6.5 inches from left to right. The typical dimension and ranges are required based on the normal size of a human face. The outer range of the measurements for the size of face covering structures 1 are for very small or very large faces.

Markings can be any color. A preferred marking color is black. Another preferred marking color is green. Bright colors can also be used on different embodiments. Bright colors will increase overall visibility of the markings. A marking which is high contrast from the face covering structure 1 is preferred for greater visibility. A high contrast color combination is a dark colored marking and a light colored outer surface of the face covering structure 1, such as a black marking and a white outer surface of the face covering structure 1. Another high contrast color combination is a light colored marking and a dark colored outer surface of the face covering structure 1, such as light blue marking and a dark red outer surface of the face covering structure.

Generally, visibility is maximized when the element viewed is larger and separated from another object. When viewing a traditional eye test chart to determine visual acuity, the large E on the top is most visible because each limb of the letter is large and separated from the other limbs of the letter. The larger the limbs of the letter and the farther distance of separation of the limbs from each other, allows greatest visibility of the letter compared to smaller letters on the traditional eye test chart.

In the different embodiments of the face covering structure 1 with the outer surface with markings of letters, symbols, or numbers arranged in a pattern of top 29, left 27, right 28, and bottom 30 areas there is a functional advantage over other arrangements. The arrangement in the top 29, left 27, right 28, and bottom 30 areas allows for the letters, symbols, or numbers to be separated from each other to allow maximum visibility and transfer of information. By spreading the letters, symbols, or numbers throughout the main visible surface of the outer surface of the face covering structure 1, the letters, symbols, or numbers are more visible to an observer as separate letters, symbols, or numbers, where each marking in a particular position conveys a particular element of information, instead of a less visible set of markings which would not be either large enough to be seen, or so large the markings would not be viewed as separate and may appear as a large blurry shape. Also by spreading out the letters, symbols, or numbers each can be a larger size, to add visibility. The arrangement in the top 29, left 27, right 28, and bottom 30 areas for the markings allows for a large size and greater separation, which allows good visibility. Also with having more markings, more information can be transferred than if the amount of markings were reduced.

The embodiment in FIG. 2 allows for the markings to be spread out over the main viewable surface, the outer surface, of the face covering structure 1, which allows for the markings to be large and separated. The disadvantage is that the continuous lines for the defined marking areas can decrease visibility because the lines can be mixed, or blurred, when viewed, with the marking when an observer views the face covering structure 1 in very low visibility situations, such as from a distance. The functional advantage is that a person viewing the face covering structure 1 from particular angle where the person could not see a marking, then the observer could see a line for the defined marking area which would cue the observer that the face covering structure 1 has information related to the wearer's vaccination status and then can view the face covering structure 1 from a different angle to obtain the information on face covering structure 1.

The arrangement of the markings in the top 29, left 27, right 28, and bottom 30 areas maximizes visibility and also allows adequate display of information. The vaccine maker is generally centered so visible from either side when viewing the face covering structure 1. If the observer sees the vaccine maker, the observer can infer that at least one dose was received in a multiple dose vaccine regime.

The separation of the markings in the top 29, left 27, right 28, bottom 30 areas of the face covering structure 1 is important for maximum visibility. For a face covering structure 1 there is a distance 60 from the axis dividing the top 29 and bottom 30 areas to the topmost part 57 of the face covering structure 1. There is also a distance 58 from the axis dividing the top 29 and bottom 30 areas to the bottommost 55 part of the face covering structure 1. The top 29 area of the face covering structure 1 is the portion of the face covering structure which will fit over the bridge of the nose. The axis dividing the top 29 and bottom 30 areas is the same distance from the topmost part 57 of the face covering structure 1 and the bottommost part 55 of the face covering structure 1. There is a distance 61 from the axis dividing the left 27 and right 28 areas of the face covering structure 1 to the leftmost part 54 of the face covering structure 1. There is a distance 59 from the axis dividing the left 27 and right 28 areas of the face covering structure 1 to the rightmost part 56 of the face covering structure 1. The axis dividing the left 27 and right 28 areas of the face covering structure 1 is the same distance from the rightmost part 56 of the face covering structure 1 and the leftmost part 54 of the face covering structure 1.

The markings can be described as in the top 29, left 27, right 28, bottom 30 area of the face covering structure 1. The position of the markings can also be further described by the way a marking will not extend over a certain boundary line which is measured by a percentage of the distance between an axis and the outermost part of the face covering structure 1. A boundary line can be determined where the boundary line runs parallel to an axis and the boundary line is a distance away from the axis based on a percentage of the distance from the axis to the outer most part of the face covering structure 1. There can be four boundary lines for each marking area, a top, bottom, right, and left boundary line, which determine the location of the topmost 64, bottommost 63, rightmost 62, and leftmost 65 part of the markings.

In FIG. 7, a boundary 22 defining where a marking in the top area 29 of the face covering structure 1, could be defined by four boundary lines 20, 21, 18, 16: (1) a bottom boundary line 16 which is situated 25% of the distance 24 from the axis 19 dividing the top 29 and bottom 30 areas and the outermost part of the top part 57 of the face covering structure 1; (2) a top boundary line 18 which is situated 75% of distance 23 from the axis 19 dividing the top 29 and bottom 30 areas and outermost part of the top part 57 of the face covering structure 1; (3) a left boundary line 20 which is situated 25% of the distance 25 from the axis 31 dividing the left 27 and right 28 areas and outermost part of the left part 54 of the face covering structure 1; and (4) a right boundary line 21 which is situated 25% of the distance 26 from the axis 31 dividing the left 27 and right 28 areas and outermost part of the right part 56 of the face covering structure 1.

In FIG. 8, a boundary 44 defining where a marking in the left area 27 of the face covering structure 1, could be defined by four boundary lines 38, 20, 16, 32: (1) a bottom boundary line 32 which is situated 25% of the distance 33 from the axis 19 dividing the top 29 and bottom 30 areas and the outermost part of the bottom part 55 of the face covering structure 1; (2) a top boundary line 16 which is situated 25% of distance 24 from the axis 19 dividing the top 29 and bottom 30 areas and outermost part of the top part 57 of the face covering structure 1; (3) a left boundary line 38 which is situated 75% of the distance 36 from the axis 31 dividing the left 27 and right 28 areas and outermost part of the left part 54 of the face covering structure; and (4) a right boundary line 20 which is situated 25% of the distance 25 from the axis 31 dividing the left 27 and right 28 areas and outermost part of the left part 54 of the face covering structure 1.

In FIG. 9, a boundary 45, defining where a marking in the right area 28 of the face covering structure 1, could be defined by four boundary lines 21, 34, 16, 32: (1) a bottom boundary line 32 which is situated 25% of the distance 33 from the axis 19 dividing the top 29 and bottom 30 areas and the outermost part of the bottom part 55 of the face covering structure 1; (2) a top boundary line 16 which is situated 25% of distance 24 from the axis 19 dividing the top 29 and bottom 30 areas and outermost part of the top part 57 of the face covering structure 1; (3) a left boundary line 21 which is situated 25% of the distance 26 from the axis 31 dividing the left 27 and right 28 areas and outermost part of the right part 56 of the face covering structure 1; and (4) a right boundary line 34 which is situated 75% of the distance 35 from the axis 31 dividing the left 27 and right 28 areas and outermost part of the right part 56 of the face covering structure 1.

In FIG. 10, a boundary 43 defining where a marking in the bottom area 30 of the face covering structure, could be defined by four boundary lines 20, 21, 32, 40: (1) a bottom boundary line 40 which is situated 75% of the distance 41 from the axis 19 dividing the top 29 and bottom 30 areas and the outermost part of the bottom part 55 of the face covering structure 1; (2) a top boundary line 32 which is situated 25% of distance 33 from the axis 19 dividing the top 29 and bottom 30 areas and outermost part of the bottom part 55 of the face covering structure 1; (3) a left boundary line 20 which is situated 25% of the distance 25 from the axis 31 dividing the left 27 and right 28 areas and outermost part of the left part 54 of the face covering structure 1; and (4) a right boundary line 21 which is situated 25% of the distance 26 from the axis 31 dividing the left 27 and right 28 areas and outermost part of the right part 56 of the face covering structure 1.

A face covering structure 1 with an indication of the wearer's vaccination status can be useful for triaging patients within a medical setting. This is important if a pandemic exists and the face mask 16 indicates the vaccine status of the vaccine used to prevent the pathogen causing the pandemic. A face mask 16 with prominent markings on the outer surface provides an effective way of signaling to medical professionals of the vaccination status of patients. The information related to the vaccination status can be communicated when a person wears a face mask 16 with the markings indicating their vaccination status and enters a medical facility. The vaccination status can be determined from a distance. Then a patient can be moved to the proper area, based on the patient's vaccination status, to avoid risk to the patient themselves, other patients, or medical professionals. For instance, if the face mask 16 indicates the patient received one dose of a two dose regimen and therefore the patient is not fully vaccinated, the patient should enter an area to better protect the patient themselves, other patients, and the medical professional because without full vaccination status the patient is more likely to become infected from the pathogen related to the pandemic, or spread the pathogen related to the pandemic. If the patient wears a face mask 16 that indicates the patient is fully vaccinated then the patient can enter an area with less precautions of protecting the patient themselves, other patients, or medical professionals. Once the patient enters the proper area based on the vaccination status indicated on the outer surface of the face covering structure 1, then medical professionals can verify the vaccination status by viewing the medical record of the patient indicating the vaccine manufacturer and number of doses received. The medical record can be accessed after the medical professional determines the identity of the patient 67 so the patient's information related to their vaccination status can be viewed in the database 66. The information related to the patient's vaccination status in the database 66 is called an inputted vaccination status 68, the vaccination status which was inputted into the database. The identity of a patient 67 will show who that patient is. The identity of a patient 67 can be a patient's name or other identifying number, such as birth date, patient ID number, social security number, or a combination of elements to indicate who a person is. The data, or also called information, for viewing the vaccination status of the patient can be within a medical record 69 within the database 66 or the information can be in some other entry for the patient 69. The medical record 69 can also be in a centralized database 66, where the medical record 69 is not necessarily a medical record 69 for a particular medical institution, but compiled data about individuals and the vaccine received, including vaccine manufacturer, doses received, and dates received. The database 66 holds multiple entries 69. A medical record 69 can be considered an entry 69 in the database 66. For instance, the database 66 is a compilation of the medical records 69. The database entries 69 can be identified by the patient's identity 67. The inputted vaccination status 68 information is related to previous treatment events of a vaccine regime. If the patient's identity 67 is entered then the database will return 70 the information related to the patient's inputted vaccination status 68 as indicated in the database 66, which is called the returned inputted vaccination status 72. If the vaccination status which is indicated on the patient's face mask 73 is not the same as the returned inputted vaccination status 72, then the patient can be moved to a different location in the medical facility. The steps of moving a patient and verifying the vaccination status can be called triaging and verifying the triaging. A single medical professional can do all the steps of the triaging and verifying the triaging. Or, more than one medical professional can do one or more steps of the triaging and verification of the triaging. Normally a medical professional will perform the actions of triaging and verifying the triaging, although the actions can be performed by another person, or other technology like a system of a camera, a computer, and other electronic equipment.

The ability to determine the vaccination status of another person at a distance is an advantage. The ability to determine the vaccination status of another person at 6 feet or farther is critical is some situations because the recommended distance of separation between people is 6 feet or farther to prevent of the spread of the COVID-19 virus.

The invention claimed is:

1. A face mask, the face mask is configured to be worn on a human face of a person called a wearer, the face mask displays a set of information about a COVID-19 vaccination regime received by the wearer, the set of information about the COVID-19 vaccination regime received by the wearer consists of a vaccine maker and a number of doses received by the wearer, comprising,
    a face covering securing structure,
    a face covering structure,
        the face covering securing structure is attached to the face covering structure,
        the face covering structure has an outer surface and an inner surface,
            the outer surface has a top, left, right, and bottom area,
            the outer surface is the color white,
    a first marking, the first marking is a letter or two letters, the first marking is on the outer surface in the top area, the first marking indicates the vaccine maker of the COVID-19 vaccination regime received by the wearer, the first marking is the color green,
    a second marking, the second marking is a check mark, the second marking is on the outer surface in the left area, the second marking indicates the first dose of the COVID-19 vaccination regime received by the wearer, the second marking is the color green,
    the outer surface has a total surface area,
    the first and second marking each cover a surface area of the outer surface,
    the first and second marking each cover the surface area of at least 5 percent of the total surface area of the outer surface,
    the face covering structure has an axis dividing the top and bottom area,
    the face covering structure has an axis dividing the right and left area,
    an outermost part of the face covering structure on the top, left, right, and bottom,
    a distance from the axis dividing the top and bottom area to the outermost part of the top and bottom of the face covering structure,
    a distance from the axis dividing the right and left area to the outermost part of the right and left of the face covering structure,
    a topmost, bottommost, rightmost, and leftmost part of the first and second markings,
    the topmost part of the first marking does not extend any farther to the top than 75% of the distance from the axis dividing the top and bottom area to the outermost part of the top of the face covering structure, the bottommost part of the first marking does not extend any closer to the axis dividing the top and bottom area than 25% of the distance from the axis dividing the top and bottom area to the outermost part of the top of the face covering structure, the rightmost part of the first marking does not extend any farther to the right than 25% of the distance from the axis dividing the right and left area to the outermost part of the right of the face covering structure, the leftmost part of the first marking does not extend any farther to the left than 25% of the distance from the axis dividing the right and left area to the outermost part of the left of the face covering structure,
    the leftmost part of the second marking does not extend any farther to the left than 75% of the distance from the axis dividing the right and left area to the outermost part of the left of the face covering structure, the rightmost part of the second marking does not extend any closer to the axis dividing the right and left area than 25% of the distance from the axis dividing the right and left area to the outermost part of the left of the face covering structure, the topmost part of the second marking does not extend any farther to the top than 25% of the distance from the axis dividing the top and bottom area to the outermost part of the top of the face covering structure, the bottommost part of the second marking does not extend any farther to the bottom than 25% of the distance from the axis dividing the top and bottom area to the outermost part of the bottom of the face covering structure.

2. The face mask as in claim 1, further comprising a third marking, the third marking is a check mark, the third marking is on the outer surface in the right area, the third marking indicates the second dose of the COVID-19 vaccination regime received by the wearer, the third marking is the color green,
    the third marking covers a surface area of the outer surface,
    the third marking covers a surface area of at least 5 percent of the total surface area of the outer surface,
    a topmost, bottommost, rightmost, and leftmost part of the third marking,
    the rightmost part of the third marking does not extend any farther to the right than 75% of the distance from the axis dividing the right and left area to the outermost part of the right of the face covering structure, the leftmost part of the third marking does not extend any closer to the axis dividing the right and left area than 25% of the distance from the axis dividing the right and left area to the outermost part of the right of the face covering structure, the topmost part of the third marking does not extend any farther to the top than 25% of the distance from the axis dividing the top and bottom area to the outermost part of the top of the face covering structure, the bottommost part of the third marking does not extend any farther to the bottom than 25% of the distance from the axis dividing the top and bottom area to the outermost part of the bottom of the face covering structure.

3. The face mask as in claim 2, further comprising a fourth marking, the fourth marking is a check mark, the fourth marking is on the outer surface in the bottom area, the fourth marking indicates the third dose of the COVID-19 vaccination regime received by the wearer, the fourth marking is the color green, the fourth marking covers a surface area of the outer surface, the fourth marking covers a surface area of at least 5 percent of the total surface area of the outer surface, a topmost, bottommost, rightmost, and leftmost part of the fourth markings, the bottommost part of the fourth marking does not extend any farther to the bottom than 75% of the distance from the axis dividing the top and bottom area to the outermost part of the bottom of the face covering structure, the topmost part of the fourth marking does not extend any closer to the axis dividing the top and bottom area than 25% of the distance from the axis dividing the top and bottom area to the outermost part of the bottom of the face covering structure, the rightmost part of the fourth marking does not extend any farther to the right than 25% of the distance from the axis dividing the right and left area to the outermost part of the right of the face covering structure, the leftmost part of the fourth marking does not extend any farther to the left than 25% of the distance from the axis dividing the right and left area to the outermost part of the left of the face covering structure.

4. The face mask as in claim 3,
the face covering securing structure is a loop, loops, a tie, ties, a strap, or straps,
the face covering structure is a flexible molded dome, a pleated paper rectangle, or a fabric rectangle.

5. The face mask as in claim 2,
the face covering securing structure is a loop, loops, a tie, ties, a strap, or straps,
the face covering structure is a flexible molded dome, a pleated paper rectangle, or a fabric rectangle.

6. A method of a patient wearing a face mask comprising,
the face mask is worn on the face of the patient,
the face mask displays a set of information about a COVID-19 vaccination regime received by the patient,
the set of information about the COVID-19 vaccination regime received by the patient consists of a vaccine maker and a number of doses received by the patient,
the face mask comprising,
  a face covering securing structure,
  a face covering structure,
  the face covering securing structure is attached to the face covering structure,
  the face covering structure has an outer surface and an inner surface,
  the outer surface has a top, left, right, and bottom area,
  the outer surface is the color white,
  a first marking, the first marking is a letter or two letters, the first marking is on the outer surface in the top area, the first marking indicates the vaccine maker of the COVID-19 vaccination regime received by the patient, the first marking is the color green,
  a second marking, the second marking is a check mark, the second marking is on the outer surface in the left area, the second marking indicates the first dose of the COVID-19 vaccination regime received by the patient, the second marking is the color green,
  a third marking, the third marking is a check mark, the third marking is on the outer surface in the right area, the third marking indicates the second dose of the COVID-19 vaccination regime received by the patient, the third marking is the color green,
  a fourth marking, the fourth marking is a check mark, the fourth marking is on the outer surface in the bottom area, the fourth marking indicates the third dose of the COVID-19 vaccination regime received by the patient, the fourth marking is the color green,
the outer surface has a total surface area,
the first, second, third, and fourth marking each cover a surface area of the outer surface,
the first, second, third, and fourth marking each cover the surface area of at least 5 percent of the total surface area of the outer surface,
the face covering structure has an axis dividing the top and bottom area,
the face covering structure has an axis dividing the right and left area,
an outermost part of the face covering structure on the top, left, right, and bottom,
a distance from the axis dividing the top and bottom area to the outermost part of the top and bottom of the face covering structure,
a distance from the axis dividing the right and left area to the outermost part of the right and left of the face covering structure,
a topmost, bottommost, rightmost, and leftmost part of the first, second, third, and fourth markings,
the topmost part of the first marking does not extend any farther to the top than 75% of the distance from the axis dividing the top and bottom area to the outermost part of the top of the face covering structure, the bottommost part of the first marking does not extend any closer to the axis dividing the top and bottom area than 25% of the distance from the axis dividing the top and bottom area to the outermost part of the top of the face covering structure, the rightmost part of the first marking does not extend any farther to the right than 25% of the distance from the axis dividing the right and left area to the outermost part of the right of the face covering structure, the leftmost part of the first marking does not extend any farther to the left than 25% of the distance from the axis dividing the right and left area to the outermost part of the left of the face covering structure,
the leftmost part of the second marking does not extend any farther to the left than 75% of the distance from the axis dividing the right and left area to the outermost part of the left of the face covering structure, the rightmost part of the second marking does not extend any closer to the axis dividing the right and left area than 25% of the distance from the axis dividing the right and left area to the outermost part of the left of the face covering structure, the topmost part of the second marking does not extend any farther to the top than 25% of the distance from the axis dividing the top and bottom area to the outermost part of the top of the face covering structure, the bottommost part of the second marking does not extend any farther to the bottom than 25% of the distance from the axis dividing the top and bottom area to the outermost part of the bottom of the face covering structure,
the rightmost part of the third marking does not extend any farther to the right than 75% of the distance from the axis dividing the right and left area to the outermost part of the right of the face covering structure, the leftmost part of the third marking does not extend any closer to the axis dividing the right and left area than 25% of the distance from the axis dividing the right and left area to the outermost part of the right of the face covering structure, the topmost part of the third marking does not extend any farther to the top than 25% of the distance from the axis dividing the top and bottom area to the outermost part of the top of the face covering structure, the bottommost part of the third marking does not extend any farther to the bottom than 25% of the distance from the axis dividing the top and bottom area to the outermost part of the bottom of the face covering structure, the bottommost part of the fourth marking does not extend any farther to the bottom than 75% of the distance from the axis dividing the top and bottom area to the outermost part of the bottom of the face covering structure, the topmost part of the fourth marking does not extend any closer to the axis dividing the top and bottom area than 25% of the distance from the axis dividing the top and bottom area to the outermost part of the bottom of the face covering structure, the rightmost part of the fourth marking does not extend any farther to the right than 25% of the distance from the axis dividing the right and left area to the outermost part of the right of the face covering structure, the leftmost part of the fourth marking does not extend any farther to the left than 25% of the distance from the axis dividing the right and left area to the outermost part of the left of the face covering structure, a medical facility, a plurality of different areas in the medical facility which allow certain patients based on the COVID-19 vaccination status of the patient, the patient enters the medical facility, observing the patient from a distance of greater than 6 feet, determining the area of the medical facility acceptable for the patient based on the area of the medical facility which allows patients in the area of the medical facility which matches the COVID-19 vaccination status indicated on the outer surface of the face mask.

7. The method of a patient wearing a face mask as in claim 6, further comprising, moving the patient to the area of the medical facility acceptable for the patient based on the area of the medical facility which allows patients in the area of the medical facility which matches the COVID-19 vaccination status indicated on the outer surface of the face mask.

8. A method of a person wearing a face mask comprising, the face mask is worn on the face of the person, the face mask displays a set of information about a COVID-19 vaccination regime received by the person, the set of information about the COVID-19 vaccination regime received by the person consists of a vaccine maker and a number of doses received by the person, the face mask comprising, a face covering securing structure, a face covering structure, the face covering securing structure is attached to the face covering structure, the face covering structure has an outer surface and an inner surface, the outer surface has a top, left, right, and bottom area, the outer surface is the color white, a first marking, the first marking is a letter or two letters, the first marking is on the outer surface in the top area, the first marking indicates the vaccine maker of the COVID-19 vaccination regime received by the person, the first marking is the color green, a second marking, the second marking is a check mark, the second marking is on the outer surface in the left area, the second marking indicates the first dose of the COVID-19 vaccination regime received by the person, the second marking is the color green, a third marking, the third marking is a check mark, the third marking is on the outer surface in the right area, the third marking indicates the second dose of the COVID-19 vaccination regime received by the person, the third marking is the color green, a fourth marking, the fourth marking is a check mark, the fourth marking is on the outer surface in the bottom area, the fourth marking indicates the third dose of the COVID-19 vaccination regime received by the person, the fourth marking is the color green, the outer surface has a total surface area, the first, second, third, and fourth marking each cover a surface area of the outer surface, the first, second, third, and fourth marking each cover the surface area of at least 5 percent of the total surface area of the outer surface, the face covering structure has an axis dividing the top and bottom area, the face covering structure has an axis dividing the right and left area, an outermost part of the face covering structure on the top, left, right, and bottom, a distance from the axis dividing the top and bottom area to the outermost part of the top and bottom of the face covering structure, a distance from the axis dividing the right and left area to the outermost part of the right and left of the face covering structure, a topmost, bottommost, rightmost, and leftmost part of the first, second, third, and fourth markings, the topmost part of the first marking does not extend any farther to the top than 75% of the distance from the axis dividing the top and bottom area to the outermost part of the top of the face covering structure, the bottommost part of the first marking does not extend any closer to the axis dividing the top and bottom area than 25% of the distance from the axis dividing the top and bottom area to the outermost part of the top of the face covering structure, the rightmost part of the first marking does not extend any farther to the right than 25% of the distance from the axis dividing the right and left area to the outermost part of the right of the face covering structure, the leftmost part of the first marking does not extend any farther to the left than 25% of the distance from the axis dividing the right and left area to the outermost part of the left of the face covering structure, the leftmost part of the second marking does not extend any farther to the left than 75% of the distance from the axis dividing the right and left area to the outermost part of the left of the face covering structure, the rightmost part of the second marking does not extend any closer to the axis dividing the right and left area than 25% of the distance from the axis dividing the right and left area to the outermost part of the left of the face covering structure, the topmost part of the second marking does not extend any farther to the top than 25% of the distance from the axis dividing the top and bottom area to the outermost part of the top of the face covering structure, the bottommost part of the second marking does not extend any farther to the bottom than 25% of the distance from the axis dividing the top and bottom area to the outermost part of the bottom of the face covering structure, the rightmost part of the third marking does not extend any farther to the right than 75% of the distance from the axis dividing the right and left area to the outermost part of the right of the face covering structure, the leftmost part of the third marking does not extend any closer to the axis dividing the right and left area than 25% of the distance from the axis dividing the right and left area to the outermost part of the right of the face covering structure, the topmost part of the third marking does not extend any farther to the top than 25% of the distance from the axis dividing the top and bottom area to the outermost part of the top of the face covering structure, the bottommost part of the third marking does not extend any farther to the bottom than 25% of the distance from the axis dividing the top and bottom area to the outermost part of the bottom of the face covering structure, the bottommost part of the fourth marking does not extend any farther to the bottom than 75% of the distance from the axis dividing the top and bottom area to the outermost part of the bottom of the face covering structure, the topmost part of the fourth marking does not extend any closer to the axis dividing the top and bottom area than 25% of the distance from the axis dividing the top and bottom area to the outermost part of the bottom of the face covering structure, the rightmost part of the fourth marking does not extend any farther to the right than 25% of the distance from the axis dividing the right and left area to the outermost part of the right of the face covering structure, the leftmost part of the fourth marking does not extend any farther to the left than 25% of the distance from the axis dividing the right and left area to the outermost part of the left of the face covering structure.

\* \* \* \* \*